US009297256B2

(12) United States Patent
Nettleton et al.

(10) Patent No.: US 9,297,256 B2
(45) Date of Patent: *Mar. 29, 2016

(54) INTEGRATED AUTOMATION SYSTEM WITH PICTURE COMPILATION SYSTEM

(75) Inventors: Eric Nettleton, Research (AU); Ross Hennessy, Budgewoi (AU); Hugh Durrant-Whyte, Rozelle (AU); Ali Haydar Göktogan, Belrose (AU); Peter James Hatherly, Lavender Bay (AU); Fabio Tozeto Ramos, Erskineville (AU)

(73) Assignee: The University of Sydney, The University of Sydney, New South Wales (AU)

( * ) Notice: Subject to any disclaimer, the term of this patent is extended or adjusted under 35 U.S.C. 154(b) by 437 days.

This patent is subject to a terminal disclaimer.

(21) Appl. No.: 13/318,465

(22) PCT Filed: Apr. 30, 2010

(86) PCT No.: PCT/AU2010/000498
§ 371 (c)(1),
(2), (4) Date: Nov. 1, 2011

(87) PCT Pub. No.: WO2010/124339
PCT Pub. Date: Nov. 4, 2010

(65) Prior Publication Data
US 2012/0046927 A1 Feb. 23, 2012

(30) Foreign Application Priority Data
May 1, 2009 (AU) ................................ 2009901932

(51) Int. Cl.
*E02F 9/20* (2006.01)
*E21C 41/26* (2006.01)
(Continued)

(52) U.S. Cl.
CPC ................. *E21C 41/26* (2013.01); *E02F 9/205* (2013.01); *A61B 2019/2207* (2013.01); *E21F 17/00* (2013.01); *G05B 2219/45004* (2013.01); *G05D 2201/021* (2013.01)

(58) Field of Classification Search
None
See application file for complete search history.

(56) References Cited

U.S. PATENT DOCUMENTS 4,104,512 A 8/1978 Strayer
4,987,540 A 1/1991 Luke, Jr.
(Continued)

FOREIGN PATENT DOCUMENTS

AU 2009901933 5/2009
AU 2009901934 5/2009
(Continued)

OTHER PUBLICATIONS

PCT International Search Report for PCT Counterpart Application No. PCT/AU2010/000498 containing Communication relating to the Results of the International Search Report, 4 pgs., (Jul. 20, 2010).
(Continued)

*Primary Examiner* — Kibrom K Gebresilassie
(74) *Attorney, Agent, or Firm* — Blakely, Sokoloff, Taylor & Zafman LLP

(57) ABSTRACT

Methods and systems are described for generating a data representation of a geographical region as an adjunct to conducting autonomous operations within the region. The method comprises receiving information specifying a plurality of localized caused zones having operation-defined geographical boundaries within the region; receiving heterogeneous data descriptive of the region; associating the received data with respective localized zones; fusing the received data associated with the localized zones into data representations of the localized zones; and integrating the data representations of the localized zones into a common data representation of the geographical region.

15 Claims, 20 Drawing Sheets

(51) Int. Cl.
*A61B 19/00* (2006.01)
*E21F 17/00* (2006.01)

(56) References Cited

U.S. PATENT DOCUMENTS

| | | | | |
|---|---|---|---|---|
| 5,111,401 A * | 5/1992 | Everett et al. | | 701/24 |
| 5,367,456 A | 11/1994 | Summerville et al. | | |
| 5,633,946 A * | 5/1997 | Lachinski et al. | | 382/103 |
| 5,823,481 A | 10/1998 | Gottschlich | | |
| 5,825,981 A | 10/1998 | Matsuda | | |
| 5,902,351 A * | 5/1999 | Streit et al. | | 701/446 |
| 5,944,764 A * | 8/1999 | Henderson et al. | | 701/50 |
| 5,987,379 A | 11/1999 | Smith | | |
| 6,608,913 B1 | 8/2003 | Hinton et al. | | |
| 6,622,090 B2 * | 9/2003 | Lin | | 701/472 |
| 6,633,800 B1 * | 10/2003 | Ward et al. | | 701/2 |
| 6,681,175 B2 | 1/2004 | MacPhail et al. | | |
| 6,792,353 B2 * | 9/2004 | Lin | | 701/454 |
| 6,799,100 B2 * | 9/2004 | Burns | | G08G 1/207 340/436 |
| 6,885,863 B2 | 4/2005 | Parkman et al. | | |
| 6,937,935 B2 * | 8/2005 | Sato | | 701/446 |
| 6,975,923 B2 * | 12/2005 | Spriggs | | 700/245 |
| 7,136,748 B2 * | 11/2006 | Umezu et al. | | 701/532 |
| 7,526,492 B2 * | 4/2009 | Mikuriya et al. | | 701/454 |
| 7,885,732 B2 * | 2/2011 | Troy et al. | | 701/2 |
| 7,933,395 B1 * | 4/2011 | Bailly et al. | | 379/201.04 |
| 7,933,929 B1 * | 4/2011 | McClendon et al. | | 707/802 |
| 7,970,532 B2 * | 6/2011 | Tehan et al. | | 701/423 |
| 8,103,438 B2 * | 1/2012 | Petrie | | B60T 7/22 340/905 |
| 8,200,423 B2 * | 6/2012 | Dietsch et al. | | 701/409 |
| 8,290,942 B2 * | 10/2012 | Jones et al. | | 707/723 |
| 8,306,726 B2 * | 11/2012 | Donnelli et al. | | 340/989 |
| 8,315,838 B2 * | 11/2012 | Durrant-Whyte et al. | | 703/1 |
| 8,326,532 B2 * | 12/2012 | Kmiecik et al. | | 701/472 |
| 8,350,849 B1 * | 1/2013 | Jones et al. | | 345/419 |
| 8,521,352 B1 * | 8/2013 | Ferguson et al. | | 701/25 |
| 8,527,199 B1 * | 9/2013 | Burnette et al. | | 701/450 |
| 8,583,313 B2 * | 11/2013 | Mian | | 701/28 |
| 8,914,225 B2 * | 12/2014 | Caskey | | G08G 1/00 701/117 |
| 8,965,578 B2 * | 2/2015 | Versteeg | | G06K 9/00664 1/1 |
| 9,056,395 B1 * | 6/2015 | Ferguson | | G06K 9/00664 1/1 |
| 9,098,086 B2 * | 8/2015 | Humphrey | | B62D 15/025 D15/25 |
| 2002/0143461 A1 | 10/2002 | Burns et al. | | |
| 2003/0060968 A1 | 3/2003 | MacPhail et al. | | |
| 2003/0100991 A1 | 5/2003 | MacPhail et al. | | |
| 2004/0139049 A1 * | 7/2004 | Hancock et al. | | 707/1 |
| 2004/0172189 A1 * | 9/2004 | Maeda | | 701/200 |
| 2004/0196163 A1 * | 10/2004 | Takenaga et al. | | 340/995.12 |
| 2004/0252288 A1 * | 12/2004 | Kacyra et al. | | 356/3.09 |
| 2005/0040232 A1 | 2/2005 | Maloney | | |
| 2005/0283294 A1 * | 12/2005 | Lehman et al. | | 701/50 |
| 2006/0075356 A1 * | 4/2006 | Faulkner et al. | | 715/782 |
| 2006/0221072 A1 * | 10/2006 | Se et al. | | 345/420 |
| 2006/0249321 A1 | 11/2006 | Cook et al. | | |
| 2007/0150149 A1 * | 6/2007 | Peterson et al. | | 701/50 |
| 2007/0168308 A1 * | 7/2007 | Wang et al. | | 706/20 |
| 2007/0271002 A1 * | 11/2007 | Hoskinson et al. | | 700/245 |
| 2008/0014965 A1 * | 1/2008 | Dennison | | H04B 7/18541 455/456.1 |
| 2008/0278311 A1 * | 11/2008 | Grange et al. | | 340/539.2 |
| 2009/0099730 A1 * | 4/2009 | McClure et al. | | 701/41 |
| 2009/0327342 A1 * | 12/2009 | Xiao et al. | | 707/104.1 |
| 2010/0076599 A1 * | 3/2010 | Jacobs | | G05D 1/0221 700/258 |
| 2010/0076631 A1 * | 3/2010 | Mian | | 701/19 |
| 2010/0256836 A1 * | 10/2010 | Mudalige | | 701/2 |
| 2010/0280699 A1 * | 11/2010 | Bageshwar et al. | | 701/26 |
| 2011/0163733 A1 * | 7/2011 | Nelson et al. | | 324/72 |
| 2011/0179176 A1 * | 7/2011 | Ravichandran et al. | | 709/226 |
| 2011/0298923 A1 * | 12/2011 | Mukae | | 348/144 |
| 2012/0044043 A1 * | 2/2012 | Nettleton | | E21C 41/26 340/3.7 |
| 2012/0046983 A1 * | 2/2012 | Nettleton | | G06Q 10/0631 705/7.12 |
| 2012/0053703 A1 * | 3/2012 | Nettleton | | E21C 41/26 700/9 |
| 2012/0053775 A1 * | 3/2012 | Nettleton | | E21C 41/26 701/24 |
| 2012/0259540 A1 * | 10/2012 | Kishore et al. | | 701/410 |
| 2012/0283905 A1 * | 11/2012 | Nakano | | G05D 1/0214 701/25 |
| 2012/0316725 A1 * | 12/2012 | Trepagnier et al. | | 701/26 |
| 2013/0016104 A1 * | 1/2013 | Morrison et al. | | 345/428 |
| 2013/0289837 A1 * | 10/2013 | Beams et al. | | 701/51 |
| 2014/0067187 A1 * | 3/2014 | Ferguson | | B60W 30/00 701/28 |

FOREIGN PATENT DOCUMENTS

| | | |
|---|---|---|
| AU | 2009901949 | 5/2009 |
| WO | WO-2004/088092 A1 | 10/2004 |
| WO | WO 2008/113098 A1 | 9/2008 |
| WO | WO 2009/027815 A2 | 3/2009 |
| WO | WO-2009/027816 A2 | 3/2009 |
| WO | WO 2009/109007 A1 | 9/2009 |
| WO | WO-2010/124335 A1 | 11/2010 |
| WO | WO-2010/124336 A1 | 11/2010 |
| WO | WO-2010/124337 A1 | 11/2010 |
| WO | WO 2010/124339 A1 | 11/2010 |

OTHER PUBLICATIONS

PCT Written Opinion of the International Searching Authority for PCT Counterpart Application No. PCT/AU2010/000498, 5 pgs., (Jul. 20, 2010).
PCT Notification concerning Transmittal of International Preliminary Report on Patentability (Chapter I of the Patent Cooperation Treaty) for PCT Counterpart Application No. PCT/AU2010/000498, 5 pgs., (Nov. 10, 2011).
Office Action for Chilean Counterpart Application No. 2711-11 with English Translation, 11 pgs. (Jun. 17, 2013).
First Office Action for Chinese Patent Application No. 201080026276.7, dated Apr. 3, 2014; 11pgs.
PCT International Search Report for PCT Application No. PCT/AU2010/000494; Jul. 15, 2010; 5pgs.
PCT Written Opinion of the International Searching Authority for PCT Application No. PCT/AU2010/000494; Jul. 15, 2010; 7pgs.
PCT Notification concerning Transmittal of International Preliminary Report on Patentability for PCT Application No. PCT/AU2010/000494; Nov 10, 2011; 10pgs.
Non-Final Office Action for U.S. Appl. No. 13/318,464, dated Jan. 29, 2014; 21pgs.
D.J Burger, "Integration of the Mining Plan in a Mining Automation System using State-of-the-Art Technology at De Beers Finsch Mine," The Journal of the South African Institute of Mining and Metallurgy; vol. 106; Aug. 2006; 8pgs.
Examiner Report for Chilean Application No. 2710-11, dated May 14, 2014; 5pgs.
Final Office Action for U.S. Appl. No. 13/318,464, dated Jul. 1, 2014; 24pgs.

* cited by examiner

INTEGRATED AUTOMATION SYSTEM WITH PICTURE COMPILATION SYSTEM

CROSS-REFERENCE TO RELATED APPLICATIONS

This patent application is a U.S. National Phase application under 35 U.S.C. §371 of International Application No. PCT/AU2010/000498, filed Apr. 30, 2010, entitled INTEGRATED AUTOMATION SYSTEM WITH PICTURE COMPILATION SYSTEM, which claims priority to Australian patent application number 2009901932, filed May. 1, 2009.

FIELD OF THE INVENTION

This invention relates to conducting integrated operations within a defined geographical region and, in particular, to operations involving autonomous equipment. The invention has various applications and, in one of its possible embodiments, has application to a mine automation system.

BACKGROUND OF THE INVENTION

There is an increasing use of control systems to automate industrial processes or machinery, as automation may provide greater efficiency and safety. As the complexity of the processes or machinery increases, the more complex the automation system becomes. This is particularly so where autonomous operations are involved.

One example of a complex application where autonomous operations may be used is in mining. Conventional open pit mining, for example of metal-bearing mineral or rock, normally involves the progressive accessing of an ore body followed by drilling, blasting, loading and haulage of the released material. In the case of iron ore it is mined in large blocks from a series of benches and the various mining activities (other than blasting) are performed concurrently, resulting in diverse equipment, and often personnel, being present simultaneously in the mine site. A bench of ore typically 40 m long×20 m deep×10 m high and containing in the order of 8 kilotonnes of ore is first drilled to form a pattern of blast holes and the drilling residue is analysed, as one step in a more extensive analysis, to determine whether the material to be blasted comprises, on average, high grade ore, low grade ore or waste material. The blasted material is collected by shovels, excavators and/or front end haul loaders, loaded into haul trucks and transported from the mine pit. The material is then processed outside of the mine pit, depending upon grade determination; waste material typically being used as mine fill, low grade ore being stockpiled or blended with high grade ore, and high grade ore being processed further as required to form a marketable product.

Autonomous operations have to date been adopted to a very limited extent on mine sites. Examples include the operation of automated haulage vehicles under remote control from centralised control systems.

SUMMARY OF THE INVENTION

According to a first aspect of the invention there is provided a method of generating a data representation of a geographical region as an adjunct to conducting autonomous operations within the region, the method comprising:
 a) receiving information specifying a plurality of localised zones having operation-defined geographical boundaries within the region;
 b) receiving heterogeneous data descriptive of the region;
 c) associating the received data with respective localised zones;
 d) fusing the received data associated with the localised zones into data representations of the localised zones; and
 e) integrating the data representations of the localised zones into a common data representation of the geographical region.

According to a second aspect of the invention there is provided an apparatus for generating a data representation of a geographical region as an adjunct to conducting autonomous operations within the region, the apparatus comprising:
 a) means for receiving information specifying a plurality of localised zones having operation-defined geographical boundaries within the region;
 b) means for receiving heterogeneous data descriptive of the region;
 c) means for associating the received data with respective localised zones;
 d) means for fusing the received data associated with the localised zones into data representations of the localised zones; and
 e) means for integrating the data representations of the localised zones into a common data representation of the geographical region.

According to a third aspect of the invention there is provided a system for generating a model of an environment in which a plurality of equipment units are deployed for the extraction of at least one resource from the environment, wherein the environment is divided into a hierarchy of localised zones having operation-defined geographical boundaries, the system comprising:
 a managing unit to configure a plurality of model compilers corresponding to the localised zones, each model compiler comprising modelling units selected from the set consisting of:
 a) a pre-extraction modelling unit configured to receive data from a first plurality of heterogeneous sensors and to fuse the data into a pre-extraction model descriptive of the corresponding localised zone;
 b) an equipment modelling unit configured to receive equipment data relating to one or more of the equipment units operating in the corresponding localised zone and to combine the equipment data into an equipment model; and
 c) a post-extraction modelling unit configured to receive data from a second plurality of sensors and to fuse the data into a post-extraction model descriptive of extracted material.

According to a further aspect of the invention there is provided a computer program comprising machine-readable code for controlling the operation of a data processing system on which the code executes to perform a method of generating a data representation of a geographical region as an adjunct to conducting autonomous operations within the region, the method comprising:
 a) receiving information specifying a plurality of localised zones having operation-defined geographical boundaries within the region;
 b) receiving heterogeneous data descriptive of the region;
 c) associating the received data with respective localised zones;
 d) fusing the received data associated with the localised zones into data representations of the localised zones; and
 e) integrating the data representations of the localised zones into a common data representation of the geographical region.

According to a further aspect of the invention there is provided a computer program product comprising machine-readable code recorded on a machine-readable recording medium for controlling the operation of a data processing system on which the code executes to perform a method of generating a data representation of a geographical region as an adjunct to conducting autonomous operations within the region, the method comprising:

a) receiving information specifying a plurality of localised zones having operation-defined geographical boundaries within the region;

b) receiving heterogeneous data descriptive of the region;

c) associating the received data with respective localised zones;

d) fusing the received data associated with the localised zones into data representations of the localised zones; and e) integrating the data representations of the localised zones into a common data representation of the geographical region.

The invention will be more fully understood from the following description of an exemplary embodiment in the form of a complete Mine Automation System (MAS). The description is provided by way of illustration and with reference to diagrammatic representations shown in the accompanying drawings.

As used herein, except where the context requires otherwise, the term "comprise" and variations of the term, such as "comprising", "comprises" and "comprised", are not intended to exclude further additives, components, integers or steps.

DETAILED DESCRIPTION OF THE EMBODIMENTS

Figure 1:
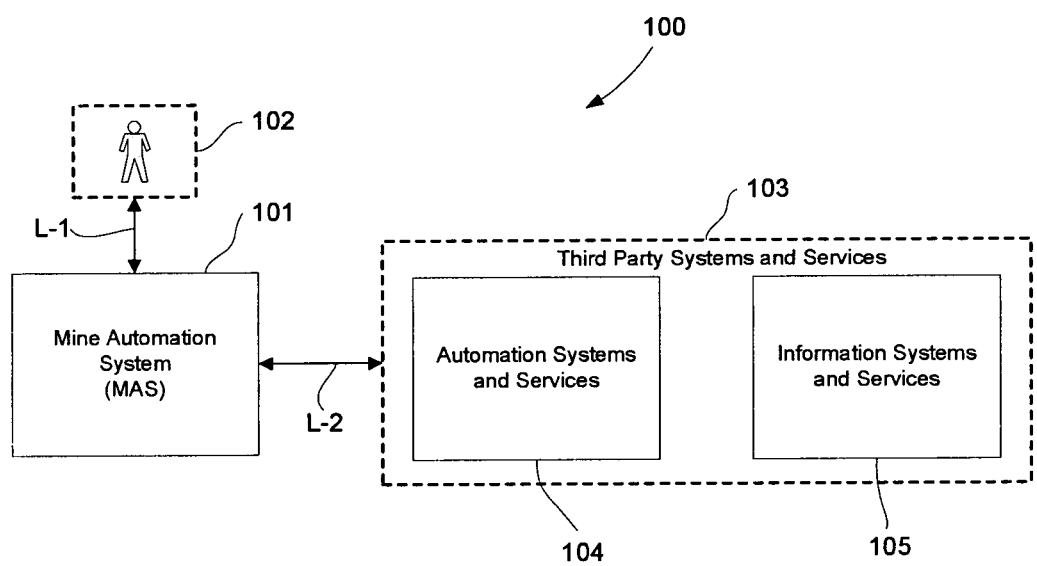
FIG. 1 is a schematic representation of a high-level architecture of an integrated automation system for a mine including an implementation of a MAS system according to one embodiment of the invention.

Broadly defined, the systems and methods described below enable autonomous operations to be effected within a defined geographical region. A plurality of localised zones having operation-defined geographical boundaries are established within the region and autonomous operating systems perform specific autonomous operations within the localised zones, the autonomous operating systems controlling one or more autonomous entities, for example self-guided and operated vehicles. An autonomous system of a management party may be integrated with the autonomous operating systems. An operator may (but need not necessarily) also be enabled to exercise overriding control over the management party autonomous system and, by way of that system, over the autonomous operating systems.

The expression "operation-defined geographical boundaries" is to be understood as meaning boundaries that embrace zones in which operations are conducted or in which operations may from time to time be conducted. For example, in the context of a mine site a boundary that embraces an active bench loading zone may be operation-defining, as may be one that surrounds a static roadway along which operational haul trucks may travel.

The described systems and methods have various applications; for example to a method of conducting autonomous operations in mining, agricultural, forestry, marine or military applications where autonomous operations may be conducted in at least one zone (that has an operation-defined geographical boundary) within a defined region. In the context of an agricultural application, for example, the invention may be employed to facilitate the implementation of controls in relation to autonomous agricultural machinery that is operated in localised zones of a larger agricultural property.

As also indicated previously, the described systems and methods may have, and in accordance with one exemplary embodiment do have, application in mining, and the invention may incorporate a mine control system ("MCS"). As such, the MCS may optionally be integrated into a mine automation system ("MAS"), with other components of the MAS optionally comprising a mine planning system ("MPS") and a mine analysis system which is referred to herein as a mine picture compilation system ("MPCS" or "MPC"). Reference may be made to Tables 12 and 13 for a listing of these and other acronyms and terminology used throughout this specification.

The system integrates operation units (third party systems of equipment deployed in the mine which may have their own automation systems), a Picture Compilation System, a Planning System and a Control System.

The MAS concept of operations entails bounded, uniquely defined localised zones or spatial regions within the mine region employing automation and/or operating personnel. Each of these zones is considered as an Island of Automation (IoA), that may effectively change location with time or whose boundary may change in shape, each operating locally with its own set of entry points, exit points, rules and constraints.

For safety, there should be strict separation between the IoAs, with an entity being only under the control of a single IoA at any given time and the described methods provide a means for controlling interactions. A combination of physical barriers, such as windows and fencing, or of virtual "barriers", such as GPS-based mapping, may be used to separate the islands/zones. As all entities in the mine will typically have a self-localisation capability, a virtual barrier can be configured to alarm or shut down operations when entities deviate from their operating regions.

At the highest level, the entire mine can be considered as a single IoA. A hierarchy of sub-regional islands can then be defined to encapsulate specific working areas. For example, separate IoAs may be created notionally within the mine for a road network, a bench to be drilled and an area under excavation. Also, it may be desirable in a given mine situation to create a nested hierarchy of smaller IoAs within these areas, should that be required. Transition into and out of an IoA is strictly controlled and the concept of a transition zone (described below with reference to FIGS. 9 and 10) is used to define the region around entry and exit points where transitions are managed. A role of these transition zones is to provide strict bounds to the areas where control handover can occur and to ensure that an entity is not operating without being under the control of an authenticated system.

The MAS and its components can be implemented in a centralised, distributed or decentralised architecture. For example, the MPC and NCS systems may be distributed or decentralised such that each IoA may have a dedicated control unit and MPC instance responsible for that IoA. The same system may also be implemented in a centralised architecture. For example the models generated by the Mine Picture Compilation System may be stored on a centralised database, or the control of all IoAs may be calculated by a centralised controller and communicated to each IoA.

The primary functional building blocks of the described systems are implemented in software. Where applicable, terminology is thus used throughout this specification to describe a software implementation.

The software required for the Picture Compilation System, Planning System and Control System may be implemented with the aid of appropriate computer hardware in the form of a computing system such as a server. The server comprises suitable components necessary to receive, store and execute appropriate computer instructions. The components may include a processing unit, memory, storage and an input-output interface. Standard computing hardware also includes a bus for communication amongst hardware components. One example of a suitable system is the Dell PowerEdge M600 server, which may be housed in a Dell PowerEdge M1000e enclosure.

The automation functionality in the operation units may be implemented using appropriate computer hardware and software. Software that needs to be run on units in harsh conditions, for example in a mine, may be run on an embedded computer that has a mounted power supply, the embedded computer comprising suitable components necessary to receive, store and execute appropriate computer instructions. The components may include a processing unit, memory, storage and an input-output interface. One example of a suitable system is the Ampro LittleBoard™800 single board computer provided by Ampro Computers, Inc of San Jose, Calif. If the automation units are deployed in harsh conditions, the computer system may be housed in a protective enclosure.

Communication between units, and between the operation units and the components of the MAS may be implemented using a wireless communication system that supports bidirectional communication.

1. Integrated Automation System

FIG. 1 illustrates a high level architecture 100 of an integrated automation system for a mine. Key elements of this system include:
Software subsystems
Embedded hardware systems
Sensor systems
Data fusion, processing and storage systems
Intelligent planning, scheduling and control subsystems
Autonomous vehicles
Communication networks.

The core element of the autonomous system is the Mine Automation System (MAS) 101, which is a distributed real-time automation system. The MAS includes interfaces, subsystems, logical connections and information dissemination links to interface and support operators and generic third party automation and information elements.

1.1. Operator Control

Human oversight of autonomous operations is an aspect of the system architecture and this is illustrated in FIG. 1, where the operator element 102 is used to encapsulate all human interaction with the MAS 101. This may include operators physically distributed throughout the mine site, at a central mine control room and at a remote operations centre, (ROC) (not shown).

The MAS architecture may be structured to allow any element in the system to be queried by human operators 102 and operator roles may be defined to allow control and monitoring of all autonomous processes, with authority to supersede automation systems or shut them down. This level of control is provided for emergency and safety cases, and desirably should not be exercised during routine operations.

Key elements of operators' roles may include:
Monitoring the status of entities in the mine;
Managing, planning and scheduling operations in the mine;
Handling and managing emergency situations;
Regulatory assessment of information systems.

1.1.1. Link L-1

Table 1 shows the information interactions between human operators 102 and the MAS 101. Information exchanges as described for all the links in the system (L-1 to L-11) are described only through the type of information that is transmitted, and not the specific message format or protocol.

The location of Link L-1 is illustrated in FIG. 1. The human operators 102 can add, edit, update or delete information in any sub-system of the MAS 101. The operators have direct interaction to the MPS 201, MCS 203 and the MPCS 202 shown in FIG. 2 and have a capability to authorise or reject data or any activity in these sub-systems.

TABLE 1

Information exchanges between the MAS 101 and human operators 102 (Link L-1).

| L-1 | |
|---|---|
| Source | Human decision makers/planners |
| Destination | Mine Automation System (MAS) |

TABLE 1-continued

Information exchanges between the MAS 101 and human operators 102 (Link L-1).

L-1

| | | |
|---|---|---|
| L-1.1 | Information to MPS. | |
| | L-1.1.1 | Information about the Mine Plan. |
| | L-1.1.2 | Information about the Job Plan. |
| | L-1.1.3 | Information about the Task Plan. |
| L-1.2 | Information to MPCS. | |
| | L-1.2.1 | Information about managing MPC instances. |
| | L-1.2.2 | Information about the Equipment Model. |
| | L-1.2.3 | Information about the In-Ground Model. |
| | L-1.2.4 | Information about the Out-of-Ground Model. |
| L-1.3 | Information to MCS. | |
| | L-1.3.1 | Information about managing xIC Instances. |
| | L-1.3.2 | Information about control plans of entities operating in the mine. |
| Source | Mine Automation System (MAS) | |
| Destination | Human decision makers/planners | |
| L-1.4 | Information from the MPS. | |
| | L-1.4.1 | Information about the Mine Plan. |
| | L-1.4.2 | Information about the Job Plan. |
| | L-1.4.3 | Information about the Task Plan. |
| L-1.5 | Information from the MPCS. | |
| | L-1.5.1 | Information about the MPCS configuration. |
| | L-1.5.2 | Information about the Equipment model. |
| | L-1.5.3 | Information about the In-Ground model. |
| | L-1.5.4 | Information about Out-of-Ground Model. |
| L-1.6 | Information from the MCS. | |
| | L-1.6.1 | Information about the MCS configuration. |
| | L-1.6.2 | Information about the status of control plans of entities operating in the mine. |

1.2. Third Party Systems

The MAS 101 architecture is arranged to support information from both existing and future systems, which may be third-party systems and services 103. This is managed through the use of flexible plug-in interface components within the system 100. The plug-ins may be written to support transformations between the representations of external systems 103 and elements of the MAS 101 and, as new systems become available, new plug-ins may be developed to ensure compatibility.

The systems 103 that interface with the MAS 101 may include information systems and services 105 and/or automation systems and services 104. An example of a third party automation system is a vehicle with its own autonomous operating system, including its own communications protocols for communicating commands to the autonomous system. Examples of third party information systems and services 105 include databases and planning systems. Some third party information systems 105 may not natively support the information formats used within the MAS 101. If required, plug-in interfaces for the MAS 101 may provide a set of transformations to convert information formats.

The MAS 101 may interface with third party automation systems and service 104 that provide specialised machinery and services such as:

Autonomous Haul Trucks;
Resource schedulers;
Specialised sensor systems and analysis methods; and
Mine-wide communication services.

The MAS 101 architecture facilitates key interface points for the integration of these third party automation systems 104. Those that meet interface specifications should integrate seamlessly.

1.2.1. Link L-2

Table 2 shows the interactions between Third Party Systems and Services 103 and the MAS 101. The location of Link L-2 is illustrated in FIG. 1. The Third Party Systems are divided into information 105 and automation 104 categories.

Information transferred to and received from Third Party Systems and Services 103 is converted to a format compatible to the MAS 101. This can be performed through native support for MAS information formats within third party systems 103, or the use of special plug-in interfaces within the MAS 101.

Third Party Systems and Services 103 can interact with the MPS 201 for planning and scheduling functions, the MPCS 202 for information fusion of geometric, geological and equipment information and the MCS 203 for control and monitoring purposes.

TABLE 2

Information exchanges between the MAS 101 and third party systems and services 103 (Link L-2).

L-2

| | | |
|---|---|---|
| Source | Mine Automation System (MAS) | |
| Destination | Third Party Systems and Services | |
| L-2.1 | Information to the Third Party Information Systems and Services | |
| | L-2.1.1 | Information about the MPCS. |
| | L-2.1.2 | Information about the MCS. |
| | L-2.1.3 | Information about the MPS. |
| L-2.2 | Information to the Third Party Automation Systems and Services | |
| | L-2.2.1 | Information about the MPCS. |
| | L-2.2.2 | Information about the MCS. |
| | L-2.2.3 | Information about the MPS. |
| Source | Third Party Systems and Services | |
| Destination | Mine Automation System (MAS) | |
| L-2.3 | Information to MPS. | |
| L-2.4 | Information to MCS. | |
| L-2.5 | Information to MPCS. | |

1.3. Mine Automation System Architecture

Figure 2:
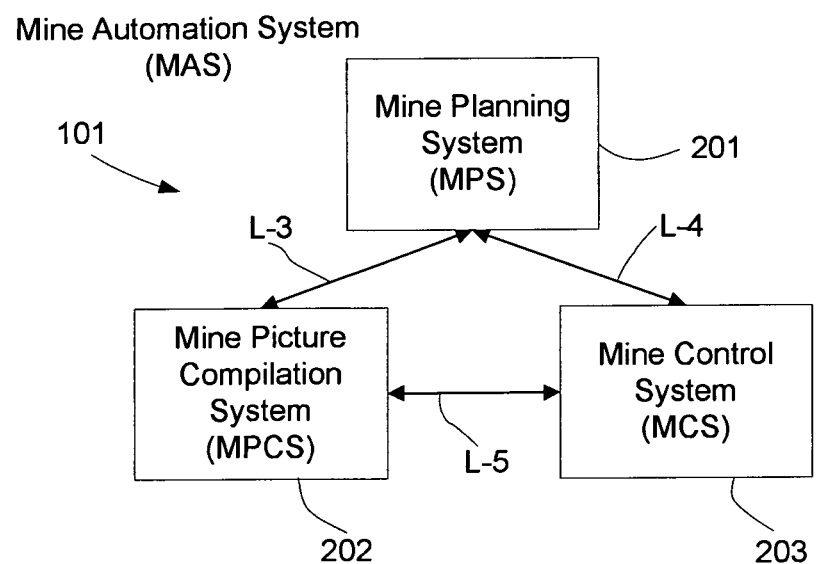
FIG. 2 illustrates the Mine Automation System (MAS) of the system of FIG. 1.

The MAS 101, shown in more detail in FIG. 2, comprises an integrated system that includes planning, estimation and control sub-systems which normally will be distributed spatially throughout a mine operation. Specifically, the main functional modules of the MAS are the:

1. Mine Planning System, MPS 201,
2. Mine Picture Compilation System MPCS, 202, and
3. Mine Control System, MCS 203.

These systems operate in a fully connected topology as illustrated in FIG. 2.

Important dependencies exist between these elements of the system; the MCS 203 having a dependency on the MPCS 202, and the MPS 201 having dependencies on both the MPCS 202 and MCS 203. Given this, the order of deployment when running the MAS 101 is:

1. MPCS 202;
2. MCS 203; then
3. MPS 201.

1.3.1. Link L-3

Information exchanges between the MPS 201 and the MPCS 202 occur through Link L-3 and are shown in Table 3. The location of this link is illustrated in FIG. 2.

TABLE 3

Information exchanges between the MPS 201 and MPCS 202 (Link L-3).

L-3

| | |
|---|---|
| Source | Mine Planning System (MPS) |
| Destination | Mine Picture Compilation System (MPCS) |

TABLE 3-continued

Information exchanges between the MPS 201 and MPCS 202 (Link L-3).

| L-3 | |
|---|---|
| L-3.1 | Information to MPC Manager. |
| | L-3.1.1  Information about managing MPC instances. |
| L-3.2 | Information to MPC instances |
| | L-3.2.1  Information about Task plans of the entities. |
| Source | Mine Picture Compilation System (MPCS) |
| Destination | Mine Planning System (MPS) |
| L-3.3 | Information to Mine Planner. |
| | L-3.3.1  Information about the MPCS configuration. |
| | L-3.3.2  Information from the Equipment Model. |
| | L-3.3.3  Information from the Out-of-Ground Model. |
| | L-3.3.4  Information from the In-Ground Model. |
| L-3.4 | Information to Job Planner. |
| | L-3.4.1  Information from the Equipment Model. |
| | L-3.4.2  Information from the Out-of-Ground Model. |
| | L-3.4.3  Information from the In-Ground Model. |
| L-3.5 | Information to Task Planner. |
| | L-3.5.1  Information from the Equipment Model. |
| | L-3.5.2  Information from the Out-of-Ground Model. |
| | L-3.5.3  Information from the In-Ground Model. |

1.3.2. Link L-4

Information exchanges between the MPS 201 and the MCS 203 occur over Link L-4 and are shown in Table 4. The location of this link is illustrated in FIG. 2.

TABLE 4

Information exchanges between the MPS 201 and MCS 203 (Link L-4).

| L-4 | |
|---|---|
| Source | Mine Planning System (MPS) |
| Destination | Mine Control System (MCS) |
| L-4.1 | Information to xIC Manager. |
| | L-4.1.1  Information about xIC configuration. |
| L-4.2 | Information to xIC Instances. |
| | L-4.2.1  Information about a Task Plan. |
| Source | Mine Control System (MCS) |
| Destination | Mine Planning System (MPS) |
| L-4.3 | Information to Mine Planner. |
| L-4.4 | Information to Job Planner. |
| L-4.5 | Information to Task Planner. |
| | L-4.5.1  Information about a Task Plan. |

1.3.3. Link L-5

Information exchanges between the MPCS 202 and the MCS 203 occur through Link L-5 and are shown in Table 5. The location of this link is illustrated in FIG. 2.

TABLE 5

Information exchanges between the MPCS 202 and MCS 203 (Link L-5).

| L-5 | |
|---|---|
| Source | Mine Picture Compilation System (MPCS) |
| Destination | Mine Control System (MCS) |
| L-5.1 | Information to xIC Manager. |
| | L-5.1.1  Information about MPC instances. |
| L-5.2 | Information to xIC Instances. |
| | L-5.2.1  Information from the Equipment Model. |
| | L-5.2.2  Information from In-Ground Model. |
| | L-5.2.3  Information from the Out-of-Ground model. |
| Source | Mine Control System (MCS) |
| Destination | Mine Picture Compilation System (MPCS) |
| L-5.3 | Information to MPC Manager. |
| | L-5.3.1  Information about MCS configuration. |
| L-5.4 | Information to MPC instances. |
| | L-5.4.1  Information about the Trajectory plans of entities. |
| | L-5.4.2  Information about the status of Tasks. |

1.3.4. MAS System Operation

Consideration is now given to the system operation and to aspects of the operation of the MAS 101, including to the system states during start-up and execution, as well as key information sequences during operation. The functional modules of the MAS 101 are shown in more detail in FIGS. 3 to 6.

The order of key operations within the MAS 101 is:

1. Create an island of automation (IoA) and its associated island controller 602, xIC. The creation of islands of automation may be a manual process, an automatic process or a combination of a manual and automatic process. A manual process may involve an operator at a user interface to the MAS 101 defining the IoA boundaries. The operator may have the assistance of the MPCS 202 in performing this role. For example, an operator may identify mining locations, roads, processing plants etc as IoAs. Automatically created IoAs may be the boundaries of a specific mining sites in which equipment must move.
2. Create a Job Planner 302 from the Mine Planner 301. This could be provided by either a human operator 102 or automatically generated by the Mine Planner 301. The human operator 102 may again use a user interface and knowledge of the capabilities of available equipment to formulate a job plan. A plan may be created for a days activities and other plans may be created for longer term activities. Information from the MPCS 202 may be used to establish jobs, for example to plan when to mine in certain locations. Some plans may be automatically generated. For example if a spillage is detected, a plan may be automatically created to assign the required clearing equipment to the location of the spillage or if a drill hole is detected as having partially collapsed, a plan for drill unit to redrill the hole formed. The plan may be formed as a 'recommendation' for a human operator, to either approve, reject or approve in modified form or may be implemented automatically, subject to an ability for operator to override the plan before or after it has commenced.
3. Create a Task Planner 303 from the Job Planner 302 for each entity identified in the job plan. Again, individual tasks may be created either manually or automatically. Generally, at the lower level tasks the amount of automation may be increased. For some tasks the mine automation system may leave the creation of sub-tasks to another autonomous control unit, for example the autonomous control unit of an individual piece of equipment.
4. The Task Planner 303 communicates plans for the entity to the top level in the xIC hierarchy 610, which passes the command down to the xIC 602 holding the entity at that time.
5. The entities execute the appropriate tasks. This may necessitate transitioning between IoAs, requesting maintenance and executing the mining operations.
6. On completion of the task, the Task Planner 303 returns its status to the Job Planner 302. The job plan is terminated when all entities in the job have completed their tasks.
7. The IoA may be deleted.

These sequences are described in more detail later in this specification.

Figure 7:
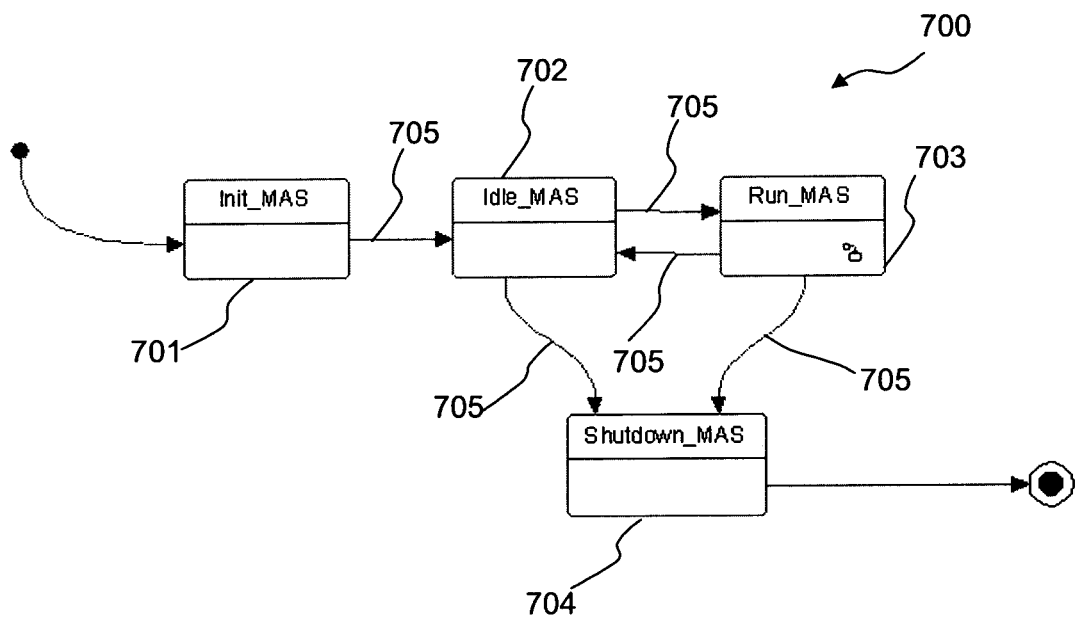
FIG. 7 is a diagrammatic representation of a high level state machine for the MAS of FIG. 2.

The top level state diagram 700 for the MAS 101 is shown in FIG. 7, illustrating the operating states and transitions 705 between them. When executed, the MAS 101 enters an initialisation state 701 where the key infrastructure is configured and launched. When successfully initialised, the MAS 101 enters an idle state 702 where it awaits commands from an operator. From this point, it will either run 703, or shutdown 704. If given the shutdown command, the underlying infrastructure for the MAS 101 is terminated. If run, the MAS 101 launches the appropriate elements.

Figure 8:
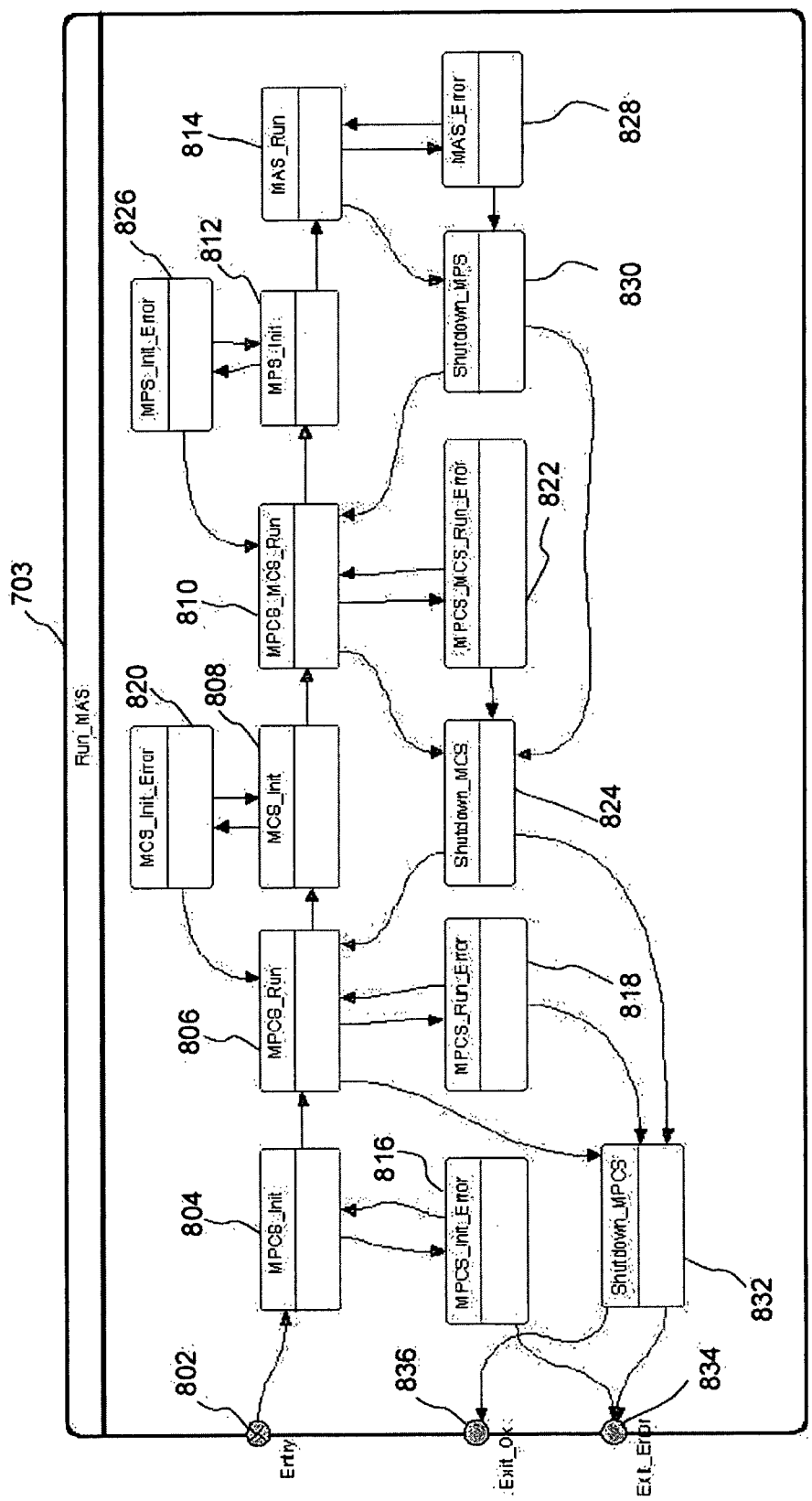
FIG. 8 is a diagrammatic representation of a state machine for a "Run_MAS" state of the state machine of FIG. 7.

The state diagram for the Run_MAS state 703 is illustrated in FIG. 8, and dependencies between. MAS subsystems are reflected in the state transitions. Upon entry 802 the system passes through an initialisation and running state for each component sequentially. MPCS initialisation 804 is followed by the running of the MPCS 806 until the MCS is initialised 808. The MPCS and MCS run state 810 leads to the initialisation of the MPS 812. With all three MAS 101 functional modules, MPS 201, MPCS 202, MCS 203 initialised, the system enters the MAS run state 814.

Any errors cause the system to revert to an error state, where it will attempt to resolve the problem and continue. In the case of an error in the MPCS initialisation state 804 the system reverts to the MPCS initialisation error state 816. In the case of an error in the MPCS run state 806 the system reverts to the MPCS run error state 818. In the case of an error in the MCS initialisation state 808 the system reverts to the MCS initialisation error state 820. In the case of an error in the MPCS and MCS run state 810 the system reverts to the MPCS and MCS run error state 822. In the case of an error in the MPS initialisation state 812 the system reverts to the MPS initialisation error state 826.

In the case of an error in the MPCS and MCS run state 810 the system reverts to the MPCS and MCS run error state 822. In this case the MCS will shut down 824, and the system will attempt to resolve the problem by returning to the MPCS run state 806.

In the case of an error in the MAS run state 814 the system reverts to the MAS run error state 828. In this case the MPS will shut down 830, and the system will attempt to resolve the problem by returning to the MPCS and MCS run state 810. If this is not possible, the system shuts down the relevant component, MCS 824 or MPS 830, and continues with reduced functionality until it is fixed, or exits with an error 834 after shutting down MPCS 832 if the error cannot be resolved.

When normal shutdown commands are issued, the system terminates each of the sub-systems in turn, MPS 830, MCS 824 and MPCS 832, and then exits cleanly 836.

1.3.5 Systems Operating Within the Mine

Various autonomous systems may be operated within a mine, and these elements interface with the MAS 101. Each of these systems will normally require a mine picture compilation (MPC) plug-in 405 for fusing their locally generated information into a global model as described below with reference to FIG. 4. Mobile entities also will normally require a plug-in 606 for an island controller 602 as described below with reference to FIG. 6, providing an appropriate motion model for trajectory planning.

Drill Automation—Auto Drilling/Rock Recognition: Drill automation may be employed to provide information on geological and geophysical rock properties on the bench at the point where a blast hole is drilled.

Drill Automation—Auto Tramming: An auto tramming sub-system for drill automation may be employed to effect automatic tramming and positioning of the drill over required hole locations specified in a drill pattern.

Haul Truck Automation: A haul truck automation system may consist of a number of haul vehicles capable of moving from point to point in the mine according to a schedule, and able to dock at a loader or shovel and to dump at the plant or waste area.

Face inspection: Automated face inspection may employ sensors to acquire relevant information at a current mining face.

Real-time Assay: Information on ore grades may be obtained autonomously from real-time or near real-time periodic chemical assays performed in the process plant.

Shovel automation: Shovel automation aims to acquire information on where excavation occurs and on what is being excavated at any given time. The information may be exploited to optimise and control the material excavation and loading process.

1.4. Mine Planning System

The MPS 201 is responsible for planning and scheduling operations within a mine. This includes short, medium and long term planning functions, and the plans within the MPS 201 may be generated either automatically or via human operators. For example, production targets in a mine may specify the quantity and quality of material that must be shipped on a monthly, weekly, and daily schedule. Given these targets, operations personnel along with mine engineers and geologists determine the sequence of blocks to mine (this is known as open pit scheduling) and the allocation of resources including mine personnel, haul trucks, shovels, drills, etc. Above this may be longer term plans spanning for example periods of 3 months, 2 years and 5 years. The longer term plans may account for factors like long-term economic forecasting and estimated mine pit total capacity.

The MPS 201 interacts with both the MPCS 202 and the MCS 203 using the information dissemination links L-3 and L-4 shown in FIG. 2. Real-time estimates of the mine provided by the MPCS 202 is the underlying model used by the Mine Planning Systems 201 for the generation and scheduling of plans. These plans are then executed using the MCS 203 at the scheduled time.

Figure 3:
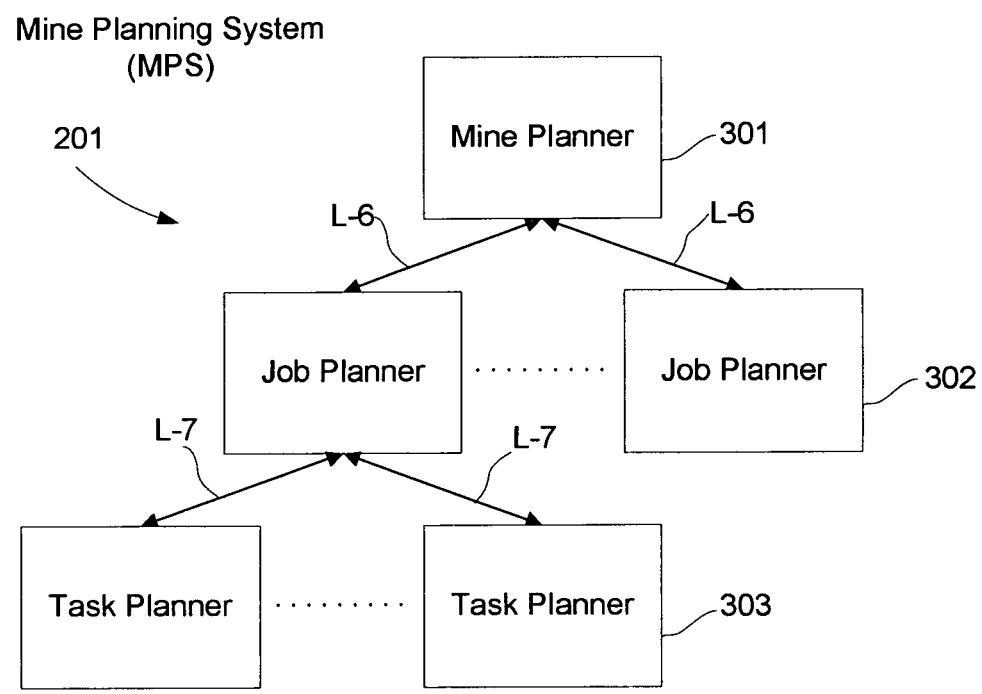
FIG. 3 is a diagrammatic representation of a Mine Planning System (MPS) of the MAS of FIG. 2.

The internal structure of the MPS 201 is illustrated in FIG. 3. This comprises a hierarchal planning system with three levels identified:

1. A Mine Plan is defined as the set of all jobs required to perform all operations in the mine, including the scheduling of equipment and/or personnel (also referred to as "entity" or "entities") to these jobs.

2. A Job Plan is a collection of one or more discrete tasks, which may require a set of either homogeneous or heterogeneous entities. The tasks are usually grouped to achieve a common goal.

3. A Task Plan is a set of discrete actions to be carried out by a specific entity.

The Mine Planner 301 is the highest level element in the planning hierarchy and is created when the MPS 201 is launched. The Mine Planner 301 performs planning operations at a strategic level across the mine.

The Mine Planner 301 uses the model of the mine created by the MPCS 202 to generate plans. Information from the model that may be used may include:

The geometry of the mine, which may be used for example to generate a dozing plan to create a road or smooth an existing road to the requirements of a vehicle required for carrying material;

Geological information, which may be used to indicate where to mine.

The Mine Planner 301 generates the plans according to a defined set of constraints. These constraints are input to the system by human operators 102, who also have oversight of any plans that are generated. The operators 102 can also modify and delete MPS 201 generated plans, and add their own. Examples of constraints that may be input include:

Timing constraints, for example when one hole in drill hole plan must be drilled before another;

Seasonal constraints, for example when certain jobs can only be completed, or only reliably or efficiently completed during certain times of the year;

Product characteristic constraints, for example where the material output from a mine should be pre-mixed so as to result in certain ore blends;

Equipment limitations, for example the capacity of equipment to carry material, movement constraints of a vehicle and the amount of equipment available to be used.

The scope of operations at this level includes planning future areas of excavation over discrete time horizons as well as planning for infrastructure work. Examples of the latter include creating plans for the construction and maintenance of roads, including regular watering, grading and inspection. When events occur that require unscheduled plans to be created, the MPS 201 can dynamically reschedule priorities and existing plans to accommodate the required actions.

The Mine Planner 301 transforms the strategic plans for the mine into a series of jobs that can be executed by specific entities. These job plans are executed by creating a Job Planner 302 at the next level in the planning hierarchy.

A functional job plan of the Job Planner 302 is created by the Mine Planner 301 for every defined job. A job plan consists of a set of separate tasks, which may require multiple heterogeneous or homogeneous entities to complete. Once created, a job plan exists until the job is either completed or deleted. Operators 102 have authority to query, modify or delete job plans as appropriate. Multiple job plans may run simultaneously The MPS 201 supports both static and dynamic allocation of entities to tasks. Static allocation refers to the case where a specific entity is pre-allocated to a specific task by a user and the entity must perform that task. Dynamic allocation refers to online rescheduling whereby a specific entity is allocated a specific task.

One high-level job planner may be a Production Planner (PP). The PP receives as input from the mine planner 301 a medium-term plan and generates jobs that can satisfy it. It associates a location and hence an IoA with each job, but not a particular vehicle that will execute it. Each generated job is passed on to a lower level job planner. For example, the PP may generate the four jobs for completion at specific locations, which may be (specified in the form job_name(Location (Loc) where job is to be completed): graderoad(Loc), pushtopsoil(Loc), pickuptopsoil(Loc), and createwaststockpile(Loc). At any time, the jobs generated are those that can be executed concurrently and/or simultaneously.

The PP must make decisions that are in compliance with the medium-term plan. A block schedule as determined in the medium-term plan and specifying the current pit shell as well as the next pit shell to be mined may be needed from the mine planner 301 for the determination of the sequence of blocks to mine. Knowledge of this schedule can be used by the PP to make rational decisions about where to construct new roads and access ramps for current and future operations. Lastly, a geometric map of the pit is a necessary input used in deciding on road/ramp construction for bench access.

The Job Planner 302 creates a separate Task Planner 303 instance for each entity defined in a job plan. If an entity type is known, but a specific entity of that type not yet allocated, the Job Planner 302 waits until a specific entity becomes available before launching that task plan. The allocation of specific entities to a task is handled by a scheduling element within the Mine Planner 301. When all task plans in a job are completed, the instance of the Job Planner 302 terminates and returns.

Each job generated by the Production Planner is passed to a lower-level job planner responsible for further refining it into a collection of tasks that can satisfy the job (depending on the level of generality that the PP operates, there may also be intermediate jobs by intermediate level job planners). Each task specifies a location and a vehicle as necessary. Tasks are selected to allow for concurrent and/or simultaneous execution. Each task is passed on to a Task Planner for further processing. In order for a job planner to create a task plan, it requires information about the availability of equipment, i.e., the total number of trucks, excavators, dozers, shovels, and graders available, as well as information about current equipment assignments, utilization, and maintenance schedules. Such information about the mine vehicles should be readily accessible via the Mine Picture Compilation System's Equipment Model.

For example, arising from the four jobs graderoad(Loc), pushtopsoil(Loc), pickuptopsoil(Loc), and createwaststockpile(Loc), then the following two tasks (amongst other tasks) may be created: pickuptopsoil(Loc; Vehicle), which takes two parameters which are the location to be processed and the vehicle that will perform the task; and load(Loc, Truck), which schedules a particular truck for loading at an excavation island.

Generally, each JP is responsible for each of the different types of operations that take place in a mine. For example, one job planner could be used for scheduling drilling and blasting operations and another for scheduling excavation jobs.

An instance of a Task Planner 303 is created by a Job Planner 302 for every entity in a job plan. It communicates directly with the MCS 203 to execute the plans on the relevant entities. The task plan may include the following information:

The target position for the entity;

A set of discrete tasks to be carried out; and

Temporal schedule for carrying out the task plan.

For example, a task planner may receive as input from a job planner the vehicle task pickuptopsoil(Loc; Vehicle) and generate a schedule of actions that would satisfy it. This schedule is passed on to the Mine Control System for execution. For example, if the Vehicle allocated by the job planner to the task pickuptopsoil(Loc; Vehicle) was truck 10 and the top soil was at location A, so that the task is pickuptopsoil(locA; truck10) an example of a sequence of actions may be navigate(locD, locB, truck10), navigate(locB, locA, truck10), service(excavator1, truck10). This schedule means that the truck will have to move from its current location locD to locA via road locB and service the excavator there. What the truck does after loading would be specified by parsing another task generated by a job planner as necessary. In the above example, subscripts denote individual locations and vehicles.

Figure 19:
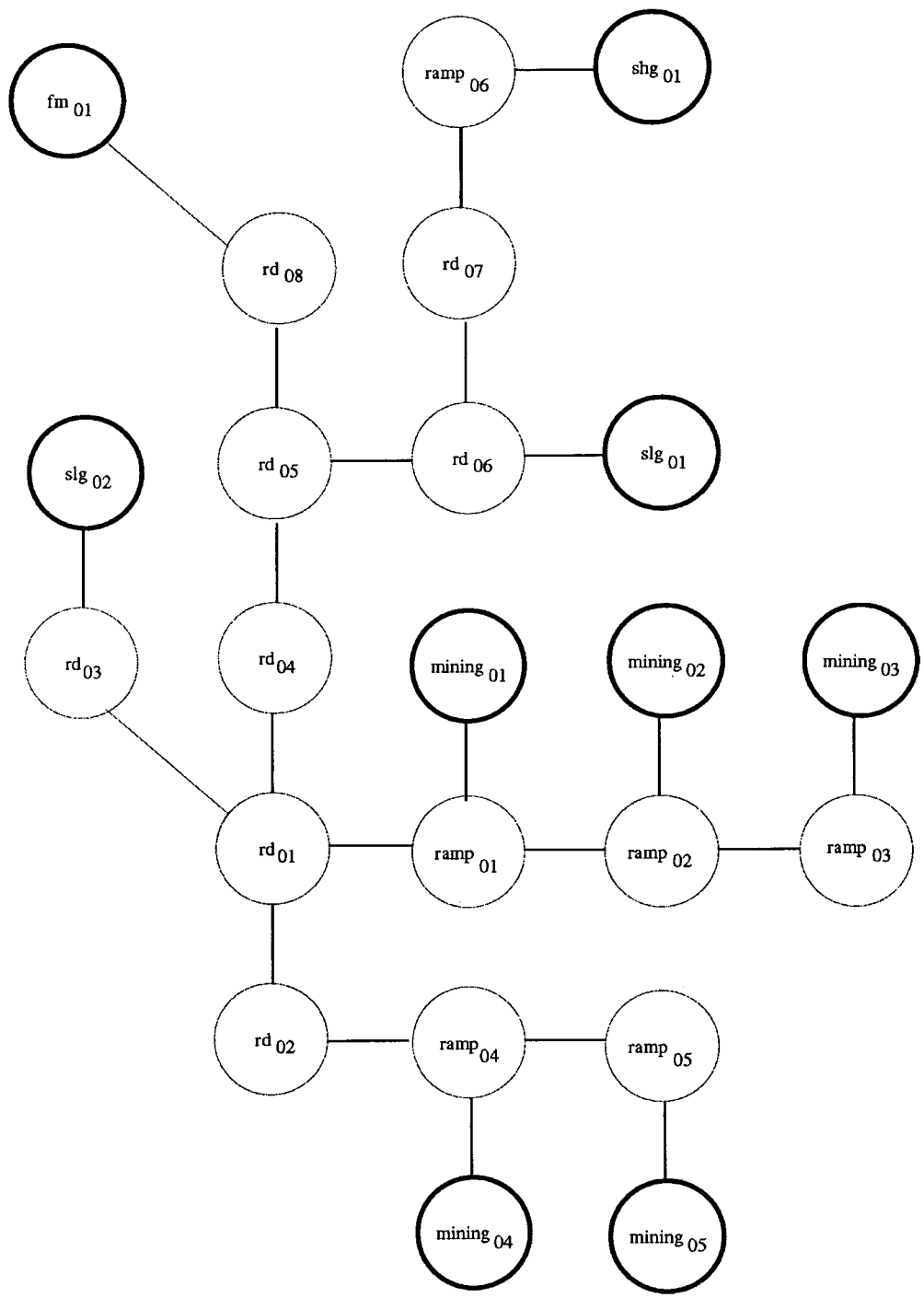
FIG. 19 is an example of a graphical representation of a geographical region.

In order to generate a task plan for each vehicle, the topological representation of the mine, as created by the MCPS by fusing sensor data, is considered. One way in which the topological representation may be considered is as a graph. FIG. 19 shows an example of representing a mine using a graph. In the graph, each vertex represents an Island of Automation. Edges between vertices shows the connectivity between IoAs. A vehicle can travel from one vertex to another if an edge connecting the two exists. The graph can be updated online such that if an unforeseen event requires the closure of a road, edges connecting to the corresponding vertex can be removed and not taken into account in generating schedules.

In addition, each edge can be marked with a weight (not shown in FIG. 19). This weight can be a function of many factors including the number of vehicles scheduled to travel between two vertices, the steepness of a road, the length of a road, the properties of the vehicles scheduled to operate in an IoA (eg. fully loaded truck, empty truck, light vehicle) and possibly others relevant to creating the best schedules that conform to the plan and ensure the safe operation of the mine. Some edges may have infinite weights denoting that even though a particular IoA is fully operational, it has reached maximum capacity. For example, safety rules may dictate that no more than 4 vehicles can share a road at the same time. As a result, if 4 vehicles have already been scheduled to navigate a particular road, an alternative path must be generated for a 5th vehicle.

Using the graph shown in FIG. 19, a schedule could be generated for a haul truck assigned the variable name truck01 currently servicing excavator $ex_{02}$ at IoA mining$_{02}$. The job may dictate that the truck must unload at the high grade stockpile $shg_{01}$. A schedule consisting of actions for this haul truck would be:

service($ex_{02}$; mining$_{02}$)

navigate(mining$_{02}$; ramp$_{02}$)

navigate(ramp$_{02}$; ramp$_{01}$)

navigate(ramp$_{01}$; $rd_{01}$)

navigate($rd_{01}$; $rd_{04}$)

navigate($rd_{04}$; $rd_{05}$)

navigate($rd_{05}$; $rd_{06}$)

navigate($rd_{06}$; $rd_{07}$)

navigate($rd_{07}$; ramp$_{06}$)

navigate(ramp$_{06}$; $shg_{01}$)

unload($shg_{01}$)

This schedule is communicated to the mine control system MCS for implementation, which will return status information.

After unloading at the high grade stockpile, the haul truck becomes available for another task which could be servicing the same excavator, another excavator, or going to the Fuelling and Maintenance hub $fm_{01}$.

1.4.1. Link L-6

Information exchanges between the Mine Planner 301 and the Job Planner 302 occur through Link L-6 and are shown in Table 6. The location of this link is illustrated in FIG. 3. All Job Planners 302 will be created by the Mine Planner 301.

TABLE 6

Information exchanges between the Mine Planner 301 and Job Planner 302 (Link L-6).

| L-6 | |
| --- | --- |
| Source | Mine Planner |
| Destination | Job Planner |
| L-6.1 | Information about Job Plans |
| Source | Job Planner |
| Destination | Mine Planner |
| L-6.2 | Information about Job Plans. |

1.4.2. Link L-7

Information exchanges between the Job Planner 302 and the Task Planner 303 occur through Link L-7 and are shown in Table 7. The location of this link is illustrated in FIG. 3. All the Task Planners 303 will be created by the Job Planner 302. A job plan may contain one or more task plans. A Task Planner 303 will exist for each entity operating in the mine.

TABLE 7

Information exchanges between the Job Planner 302 and Task Planner 303 (Link L-7).

| L-7 | |
| --- | --- |
| Source | Job Planner |
| Destination | Task Planner |
| L-7.1 | Information about the task plans of entities. |
| Source | Task Planner |
| Destination | Job Planner |
| L-7.2 | Information about task plans of entities. |

1.5. Mine Picture Compilation System

Figure 4:
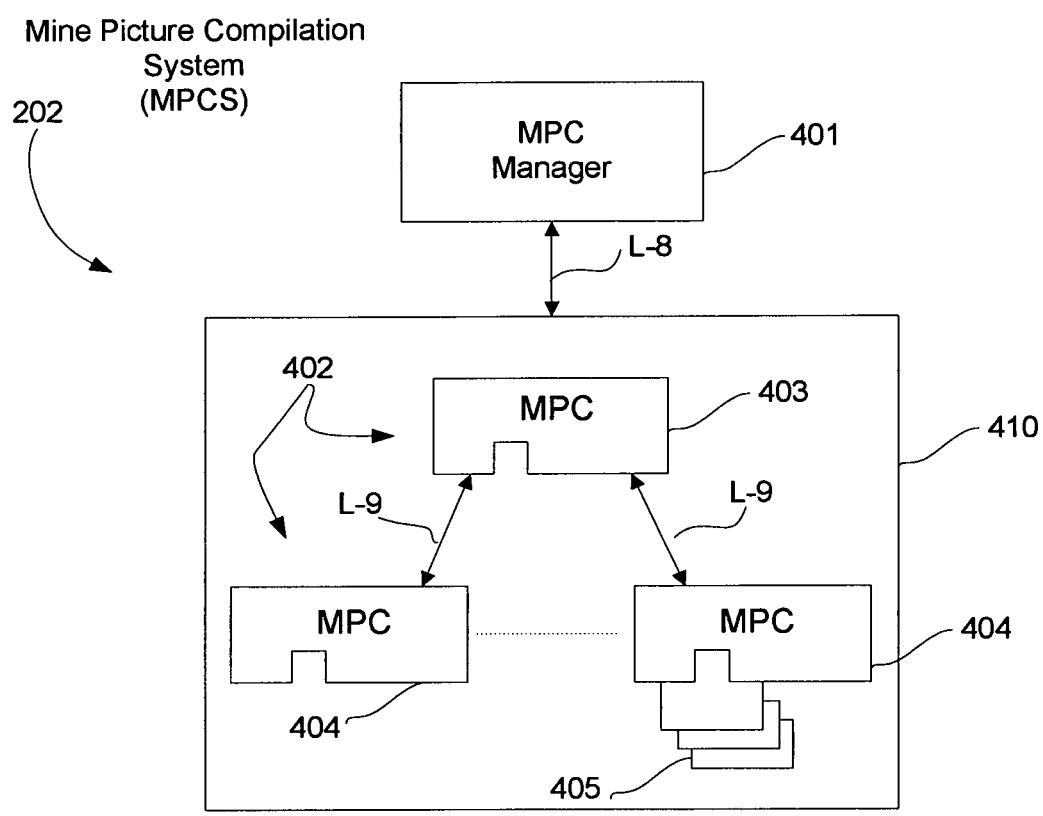
FIG. 4 is a diagrammatic representation of a Mine Picture Compilation System (MPCS) of the MAS of FIG. 2.
Figure 5:
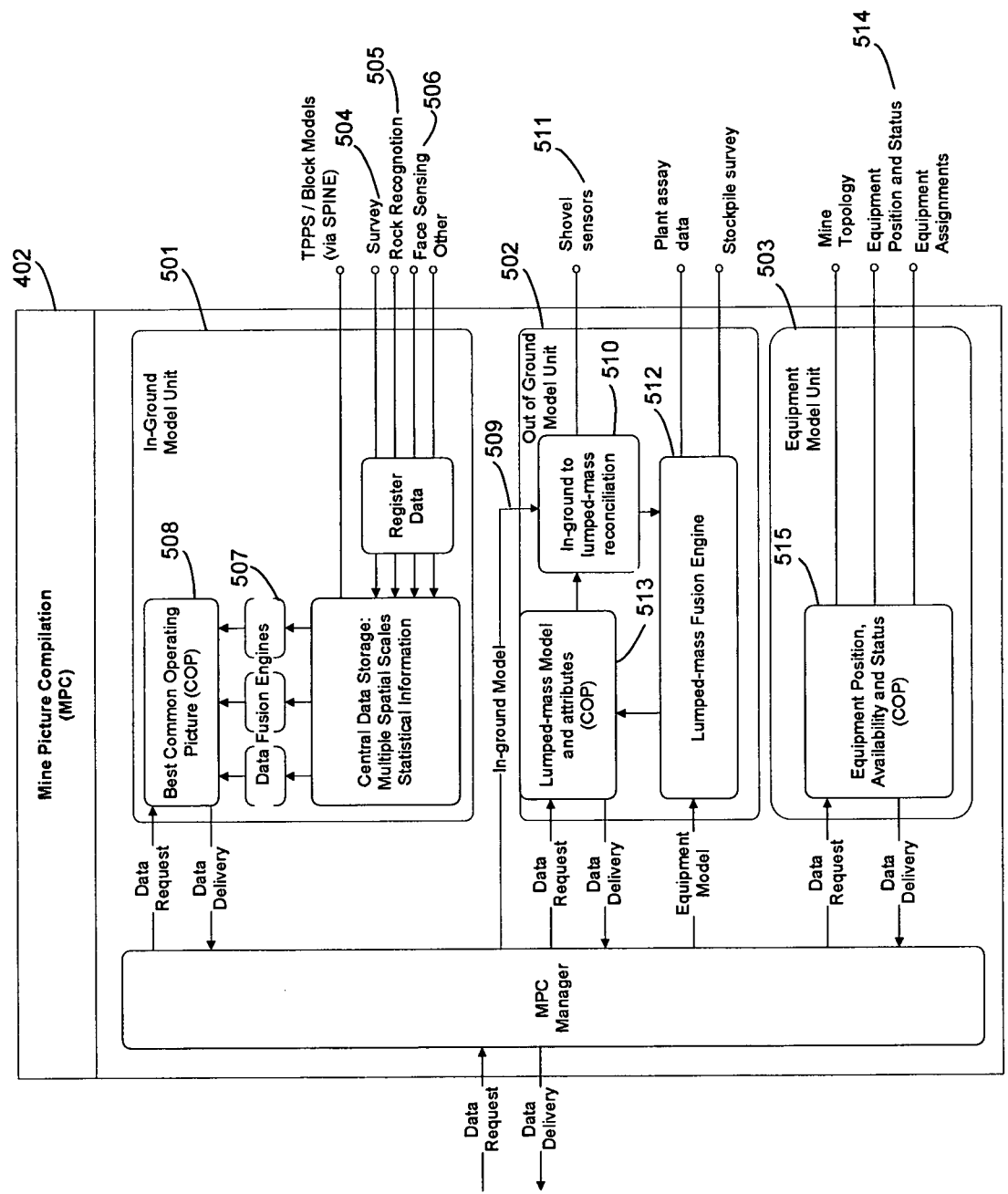
FIG. 5 shows a logical schematic of a fusion system of the MPCS of FIG. 4.

The MPCS 202 is illustrated in FIGS. 4 and 5 and it functions to integrate information from a variety of spatial, spectral and geological sensors (not shown) into a single common operating picture of the mine. This integration may be performed in real time based on information from the various sensors. The specific MPC instances described below fuse the sensor data and communicate the fused data in the hierarchy. The word "picture" is not limited to a visual image, but refers more broadly to a multi-dimensional data representation or characterisation of the mine. The data may include image data. The MPCS 202 operates at many scales and resolutions, integrating information from wide area sensors on the ground or in the air, with information from local sensors on vehicles and other platforms. In general, sensors are used in conjunction with a specific MPC instance. However, in some arrangements wide-area data may be partitioned and partitioned subsets may be associated with different MPC instances.

The MPCS 202 represents diverse types of information in a common form and it has two key elements (as shown in FIG. 4):

1. a single MPC Manager 401; and

2. MPC fusion Instances 402, including (as shown in FIG. 4) a single "parent" MPC 403 and two "child" MPC's 404 linked to the parent 403 via link L-9.

The MPC instances 402 form a hierarchy 410. Although not shown in FIG. 4, the MPC instances 402 may in appropriate situations be interconnected in any desired parent, child, etc hierarchy 410, including, for example, one having at least one "grandchild" MPC (not shown in FIG. 4) linked to one or another child MPC 404. In some embodiments there is a one-to-one relationship between the hierarchy 410 of MPC instances and the hierarchy of xIC's, with the structure of the xIC's dictating the structure of MPC instances.

Each MPC instance 402 has plug-ins 405 specific to the equipment and human operators to which it is connected. The required bandwidth of the communication channels of the MPC instances 402 in the lower level of the hierarchy will be determined by the nature of plug-ins 405 interfaced to the MPC instance 402.

MPC information is made accessible through the use of model plug-ins 405. Model plug-ins 405 are software elements that "plug-in" to the system such that they have complete access to the internal MPC information. The fusion system is then constructed using the generic MPC instance 402 as a framework, and by writing specific model plug-ins 405 that can update the underlying MPC representation for each different information type. The updating by a model plug-in 405 may occur, for example, on receipt of new sensor data or on receipt of information that indicates that equipment has changed location. The updating may occur in real-time or on a scheduled basis, or when another update trigger occurs. This architecture permits the MPCS 202 to be extended to use new information types if or when they become available without the need to rewrite any existing elements of the system.

Also, each MPC instance 402 may have any number of these plug-ins 405, each of which can perform a different task. MPC plug-ins 405 will typically include the following functions:

Read MPC state information and output to user;
Read MPC state information, transform to alternate format and output;
Update MPC models with new information about entity pose (position and orientation);
Update MPC models with new information from the rock recognition system;
Update MPC models with new information from the face inspection system;
Update MPC models with new information from third party systems.

The MPC Manager 401 is the MPCS component created when the system starts. Its function is solely to manage the network of hierarchical MPC fusion Instances 402 which may be distributed spatially throughout the mine and a remote operations centre, ROC. It does not maintain the fused information and it does not perform fusion operations.

The key responsibilities of the MPC manager 401 are to create, delete, configure and manage the network of MPC instances 402. These Instances 402 are dynamically created and managed based on information sent to the MPC manager 401.

1.5.1. Link L-8

Information exchanges between the MPC Manager 401 and the MPC instance hierarchy 410 (Parent 403 and Child 404 modules) occur through Link L-8 and are shown in Table 8. The location of this link is illustrated in FIG. 4. The MPC Manager 401 is created during the start-up operation of the system and creates MPC instances 402 whenever necessary.

The MPC Manager 401 is responsible for creating, updating and deleting of MPC instances 402. Each MPC instance 402 will be allocated with a specific address or index that is used to identify the MPC instance 402 in the MPC hierarchy 410.

TABLE 8

Information exchanges between MPC Manager 401 and MPC instance 402 (Link L-8).

| L-8 | |
|---|---|
| Source | Mine Picture Compilation Manager |
| Destination | Mine Picture Compilation (Parent Module and Child modules) |
| L-8.1 | Information about creating/updating and deleting MPC instances. |
| Source | Mine Picture Compilation (Parent Module and Child modules) |
| Destination | Mine Picture Compilation Manager |
| L-8.2 | Information about the status of MPC instances. |

The MPC instances 402 will normally be designed to be capable of supporting hierarchical topologies 410. Each MPC instance 402 will have the same properties and algorithms as its parent MPC instance 403. Child MPC instances 404 may operate on any subset of information available from their parent 403. When operating on a subset of the total information state, the requirements for bandwidth and information processing power at the child MPC instance 404 are reduced accordingly.

1.5.2. Link L-9

Information exchanges between the MPC Parent 403 and an MPC Child 404 occur through Link L-9 and are shown in Table 9. The location of this link is illustrated in FIG. 4. Both MPC Parent 403 and MPC Child 404 are created by the MPC Manager 401.

An MPC Child 404 can extract, copy or update a region of the MPCS 202 representation from its parent. Both the MPC Parent 403 and Child 404 instances may be modified or deleted by the MPC Manager 401.

TABLE 9

Information exchanges between MPC Parent 403 and MPC Child 404 (Link L-9).

| L-9 | |
|---|---|
| Source | Mine Picture Compilation (Parent) |
| Destination | Mine Picture Compilation (Child) |
| L-9.1 | MPC representations. |
| Source | Mine Picture Compilation (Child) |
| Destination | Mine Picture Compilation (Parent) |
| L-9.2 | MPC representations. |

Referring to FIG. 5, the MPC instances 402 comprise three primary models responsible for monitoring the properties of the mine. The in-ground model unit 501 maintains a multi-scale probabilistic representation of the geology and geometry of the mine. The out-of-ground model unit 502 maintains a representation of the material in process and stockpiles. The equipment model unit 503 maintains a representation of equipment.

Methods and systems for generating a model of an environment using an in-ground model, an out-of-ground model and an equipment model are described in co-assigned application titled "Method and system for exploiting information form heterogeneous sources", filed as PCT application PCT/AU2009/000265 claiming priority from an Australian provisional application filed on 4 Mar. 2008, which is incorporated herein by reference in its entirety.

The in-ground model unit 501 is responsible for maintaining and updating a multi-scale probabilistic representation of the geometry and geology of the in-ground material. Included in this model are geometric properties (walls, benches, etc), hole positions and drill patterns, geological information such as disposition of shale, Banded Iron Formation (BIF) and iron ore zones, chemical composition, and mechanical properties of these zones including rock factors and hardness.

The in-ground model unit 501 integrates information from sources such as survey 504, rock recognition 505, face inspection 506, chemical assays and exploration holes to better model and predict the geometry and geology of material in the ground. This information is spatially heterogeneous at many scales and is necessarily uncertain.

The data fusion engines 507 operate as applications on the common data base. The output of the combined fusion operation is identified as the common operating picture (COP) 508, a best estimate of all spatial and geological properties based on the combined evidence from all sources of information. Different fusion algorithms and methods are employed for different types of estimate. For example, best spatial estimates for geological structures may require the use of a Gaussian Process model which describes spatial correlations in data, best surface models can be obtained from irregular spatial tessellations, and geological class information from a discrete classifier. Using a client structure for the data fusion allows different data fusion algorithms to be incorporated into the system.

The COP 508 contains the best estimate of quantitative geometric, geological and geophysical properties, qualified with statistical confidence bounds. This information can be accessed through specific data requests from any other service provider in the mine. Data requests may originate from automated machines, such as drill rigs (that require information for purposes of control and optimal operation), individual decision makers, such as planners, who require this information to plan mining operations, or display units at local or remote sites. Different types of request need to be supported including those in restricted spatial areas or those for which data is required in real or near-real-time.

The out-of-ground model unit 502 reconciles material (as it is excavated, transported and stockpiled) with in-ground resource estimates 509 in the in-ground to lumped-mass reconciliation unit 510. The out-of-ground model unit 502 fuses information from the in-ground model unit 501 with data (from for example, shovel sensors 511) to obtain estimates of quantity and grade during material removal from the face. Fusion is performed by the Lumped-mass Fusion Engine 512. This information is propagated during haulage and reconciled with observations made by material flow measurement and assay in the plant, and further reconciled with post-plant stockpile surveys. The out-of-ground model unit 502 generates a lumped mass model 513 with associated geophysical and chemical attributes. The mass model 513 is ideally tied to the point of excavation for use in post-mining refinement of the resource model. The mass model 513 can, on demand, estimate the location and grade of all available stock in the mine. Information about unexcavated, broken stock is utilised by the in-ground model unit 501.

The out-of-ground model unit 502 describes flow from in-ground to stockpile reclaiming. Fundamentally, the model 513 must conserve mass and attributes as material flows through the system from bench to train. Each step in the process involves measurements which identify local flow characteristics. These measurements need to be fused to reconcile material conservation. Current estimates must be made available for material management and scheduling.

The equipment model unit 503 maintains and updates information 514 related to equipment location and status. Much of this information is made available through existing dispatch systems for trucks and shovels. The equipment model 515 provides an interface through which information can be exchanged between these existing systems and the MPC system 202 and in particular to enable the out-of-ground model unit 502 to reconcile material models at the bench with material flows through the plant. The equipment model 515 receives equipment position, disposition and status.

1.6. Mine Control System

Figure 6:
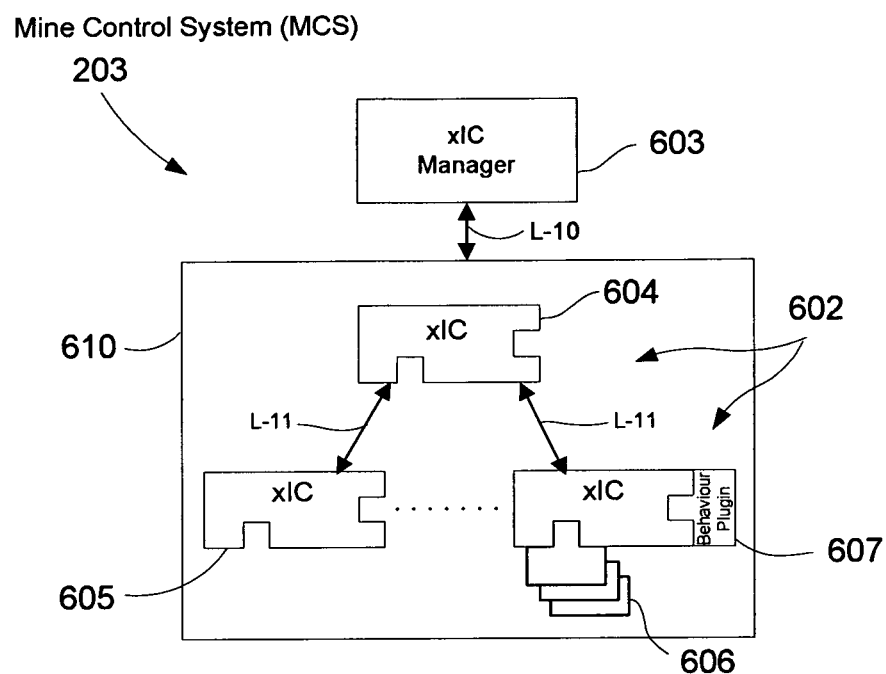
FIG. 6 is a diagrammatic representation of a Mine Control System (MCS) of the MAS of FIG. 2.

Reference is now made to the Mine Control System, (MCS) 203, as illustrated in FIG. 6. The MCS 203 functions within any required number of localised zones (referred to herein as "islands of autonomy", "islands of automation" or "IoA") that have operation-defined geographical boundaries within a defined mine region and, associated with the islands of autonomy, island controllers 602 ("xIC's" or "xIC Instances") governed by a single xIC Manager 603.

The xIC Manager 603 is created when the MCS 203 starts and its function is solely to manage the network of xIC Instances 602 which may be spatially distributed throughout the mine and ROC. It does not itself perform any control functions within the islands of automation.

The key responsibilities of the xIC Manager 603 are to create, delete, configure and manage the network 610 of xIC instances 602. These instances are dynamically created and managed based on information sent to the xIC Manager 603.

The xIC Instances 602 provide a common control system for all IoAs. Each xIC Instance 602 can be identical to all others and all are created and managed by the xIC Manager 603. As shown in FIG. 6, the xIC's 602 in the network 610 are configured in a hierarchy that is determined by the spatial location of the IoAs within the mine. The top of the hierarchy corresponds to the IoA encapsulating the entire mine, and the system then distributes recursively with the next layers respectively, with "parent" 604 and linked "child" 605 xIC's as shown in FIG. 6. There is a 1:1 mapping of xIC Instances 602 and islands of automation and, if a child IoA is created inside a functioning IoA, the parent xIC 604 will have full control over the child IoA. Similarly, if a grandchild IoA is created inside a functioning child IoA, the child xIC 605 will have full control over the grandchild IoA.

Control by the MCS 203 is hierarchical and thus the control tasks may fall into higher-level tasks and lower-level tasks. A parent xIC 604 may supervise the control tasks of a child xIC 605. An xIC may direct or supervise a control system of an autonomous entity operating within an Island of Automation. Thus for example, an autonomous vehicle may receive the higher-level command "Move to location x". The local control of the autonomous vehicle or group of autonomous vehicles may then be responsible for controlling the systems and actuators of the vehicle in order to move the vehicle(s) to the specified location. In other words, the MAS 200, through the MCS 203 is performing the operations of a management party for autonomous operations within the highest level IoA, the management party performing functions that include the job or task level control of a lower level autonomous system, which will manage its own tasks in response to the receipt of a job or higher level task command.

1.6.1. Link L-10

Information exchanges between the xIC Manager 603 and the xIC Instances 602 occur through Link L-10 and are shown in Table 10. The location of this link is illustrated in FIG. 6. The xIC Manager 603 is created when the MCS 203 is executed. The xIC Manager 603 is responsible for creating, updating and deleting xIC Instances 602. The xIC Instances 602 are responsible for controlling activities within a specific IoA.

TABLE 10

Information exchanges between xIC Manager 603 and xIC Instance 602 (Link L-10).

| L-10 | |
|---|---|
| Source | xIC Manager |
| Destination | xIC Instances (Parent Module and the Child Modules) |
| L-10.1 | Information about creating/updating and deleting of xIC Instances. |
| Source | xIC Instances (Parent Module and the Child Modules) |
| Destination | xIC Manager |
| L-10.2 | Information about the status of xIC Instances. |

1.6.2. Link L-11

Information exchanges between the xIC Parent 604 and the xIC Child 605 Instances occur through Link L-11 and are shown in Table 11. The location of this link is illustrated in FIG. 6. Both the xIC Parent 604 and xIC Child 605 are created by the xIC Manager 603.

TABLE 11

Information exchanges between xIC Parent 604 and xIC Child 605 (Link L-11).

| L-11 | |
|---|---|
| Source | Island Controller (xIC - Parent) |
| Destination | Island Controller (xIC - Child) |
| L-11.1 | Information about the task plans of entities. |
| L-11.2 | Information about registration and deregistration of entities from an Island of Automation. |
| Destination | Island Controller (xIC - Child) |
| Source | Island Controller (xIC - Parent) |
| L-11.3 | Information about task plans of entities. |
| L-11.4 | Information about registration and deregistration of entities from an Island of Automation. |

Although the core xIC Instances are all identical, each IoA can operate with different control rules, priorities or entities through the use of plug-ins. Each xIC Instance 602 has two distinct types of plug-ins, as described below, a so-called "behaviour plug-in" 607 and an "entity model plug-in" 606.

Every entity entering an IoA is first registered in the associated xIC (eg 605), the registration being coordinated by the parent xIC 604 as described in detail later in this specification.

Each xIC 602 interacts with at least one MPC instance 402 for each IoA. This is needed to obtain information from the above described in-ground model unit 501, out-of-ground model unit 502 and equipment model unit 503 to execute the tasks within the IoA.

The behaviour plug-in 607 specifies IoA-specific features, which may include the equipment that can operate in the IoA, operations which may be carried out in the IoA, type of the IoA, information about unauthorised entities and actions for the IoA and rules and regulations for performing tasks in the IoA.

The entity model plug-ins 606 serve two main purposes:
1. Being specific to a particular type of entity, a given plug-in 606 enables the xIC 602 to generate appropriate controls for the relevant entity.
2. A given plug-in 606 specifies the communication interface to the entity.

Each xIC 602 requires the appropriate entity model plug-in 606 for each entity in the IoA, and there is no limit to the number of plug-ins that can be connected at any one time.

The use of the entity model plug-in 606 to communicate to the entity means that the key control interface standard is between the plug-in 606 and the xIC 602. Separate standards may then be generated for communication to each different class of entity. The plug-in interface ensures that there is a single standard that can be common across all different classes of entities. Thus, although the information communicated between a plug-in and a drill may differ from that between a plug-in and a haul truck, the interface between the xIC 602 and both plug-ins is common.

Consideration is now given to the execution of control within the IoAs.

The hierarchy 610 of the control system 203 is deployed with software elements assigned to spatial regions of the mine, known as zones or islands of operation. The control system 203 is designed specifically to provide the flexibility to operate mixes of both human systems and autonomous systems safely within the same mine or mine region, and the following contains a description of the core functions within the MCS 203.

An operator 102 uses the MAS interface to define a new IoA, which then sends this information to the xIC Manager 603. The operator 102 is required to specify parameters such as:

Island boundaries;
Transition zones;
An MPC instance 402 to connect to;
A behaviour plug in 607; and
A physical deployment location.

Once all required parameters are set, the xIC Manager 603 creates the xIC Instance 602 according to the specifications given. The new xIC Instance 602 initiates the process of registering itself to the parent 604 in the hierarchy 610, and awaits confirmation. The parent 604 will then transition the control of all entities within the boundaries of the new island to the new xIC controller. The xIC 602 registers its MPC plug-in 405 with the specified MPC instance 402, which then confirms its status to the xIC Manager 603. The xIC Manager 603 alerts the MPCS 202 that the island exists and is active and returns the status to the operator 102.

The process of varying the geographic boundaries of an IoA is similar to the process of creating a new IoA. The variation may be instigated at various points in the system. For example, an operator may use the MAS interface to specify that a change is required. The operator specifies the revised island boundaries and, if necessary, may define one or more transition zones for the revised island.

In some arrangements there may be an automated variation of island boundaries. For example, the size of a bench may be automatically increased or decreased depending on a calculated drill pattern. In another example, the geographic boundaries of an excavation zone may be automatically increased as the excavation proceeds.

When the island boundaries change, the system may check to ensure that entities within the island before the change remain within the island after the boundary change. If an entity falls outside the island as a result of the boundary change, then control of the entity is transferred to another IoA. For example, if the boundary of xIC instance 605 is varied, control of an entity formerly within xIC 605 may be transferred to the parent xIC 604 in the hierarchy 610.

Similarly, if a change to a boundary means that an entity will fall within the boundary, then control of the entity is transferred to the xIC of the changed IoA. This transfer may require handshaking between the xIC of the varied island and the xIC of its parent.

An alternative approach to varying the boundary of an existing island is to delete the island and then to create a new island with the redefined geographical boundary.

If an IoA is to be deleted, an operator 102 sends the command to the xIC Manager 603, which then sends the deletion command to the relevant xIC instance 602. The xIC Instance 602 must pass control of all entities within its boundaries to its parent 604 in the hierarchy 610, then deregister itself from that parent 604. If successful, the instance deregisters its MPC plug in 405, confirms status to the xIC Manager 603 and terminates. The MPCS 102 and the operator 101 are alerted that the xIC 602 has been deleted. The stages in this sequence correspond with those in the creation process.

2. Transitions

Figure 9:
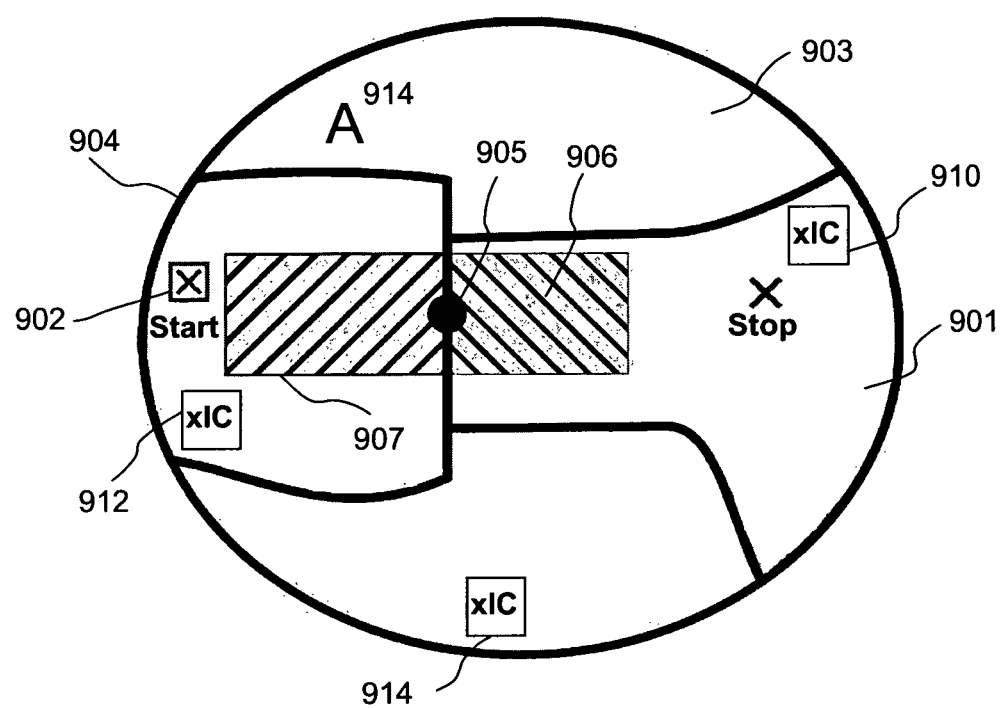
FIG. 9 illustrates a transition example for an entity seeking transition from a start location in B to an end location in C according to one embodiment of the invention.

FIG. 9 illustrates the components involved when an entity moves from one zone to another.

Transitions from and between IoAs are performed using a pull-based mechanism in which a receiving IoA 901 drives the request for an entity 902 through the parent island 903 that then coordinates with the base 904 (island currently responsible). An entity 902 is then transitioned using a double-handshake protocol. The transition occurs at a specific port 905 within transition zones 906, 907. The process has secondary control added to an entity before entry into a region and prior control authority is removed only once the entity has fully transitioned.

The general procedure is:

1. Find the lowest layer that encapsulates the entire region needed for the task required. This is considered the parent IoA 903.

2. The receiver xIC 910 (at the command of the supervising parent 903) creates a space for the receipt of the entity 902 at the requisite port 905.

3. Then the base xIC 912 (at the command of the supervising parent 903) will determine if the entity 902 can be freed and transferred to the requisite port 905.

4. The parent 903 will then coordinate (and if necessary disambiguate) the transition by commanding the base 904 to move the entity 902 to the transfer port 905 and its given transition zone 907.

5. When the entity enters the transition zone 907, the registration process begins. This is the first part of the handshake. This entails the entity 902 notifying the base xIC 912, which notifies the parent xIC 914, which notifies the receiver xIC 910. During this, the entity 902 is open to receiving forward looking operations for actions in the transition zone 906 of the receiving xIC 910. The entity 902 then receives secondary control from the receiver 901. As part of initialization to the receiving xIC 910, the entity 902 is given the geographic bounds, transition zone bounds, and travel path to execute a successful transition. Once the entity 902 has transitioned into the space 906 of the receiving xIC 910, the deregistration process begins for the base xIC 912. This is completed before leaving the receiver's transition zone 906.

The entity 902 maintains a control list through which the receiving xIC 910 obtains secondary control during the transition. A safety command takes precedence regardless of the controller issuing it.

The control architecture has been developed to be consistent with the "lockholder" policy practised in a mine site. The addition of control is analogous to adding a personal isolation lock. Thus, a control "lock" for a particular xIC can only be removed by that xIC. Further, to operate in a xIC requires the control "lock" of that xIC. Control is added and removed in the transition zones 906, 907. Thus, the receiver xIC 910 adds its control "lock" to the entity 902 while the entity is in the base's transition zone 907. On the transfer of an entity 902 to the receiver IoA 901 (and control to its xIC 910), then the base xIC 912 will "unlock" control within the transition zone 907 of the receiver.

Referring to FIGS. 10a-10e an example is shown of a transition of an entity 902, "Entity X", from a base xIC 912, "Base xIC B", to a receiver xIC 910, "Receiver xIC C", via a port 905, "Port P" as supervised by a parent xIC 914, "Parent A".

Figure 10A:
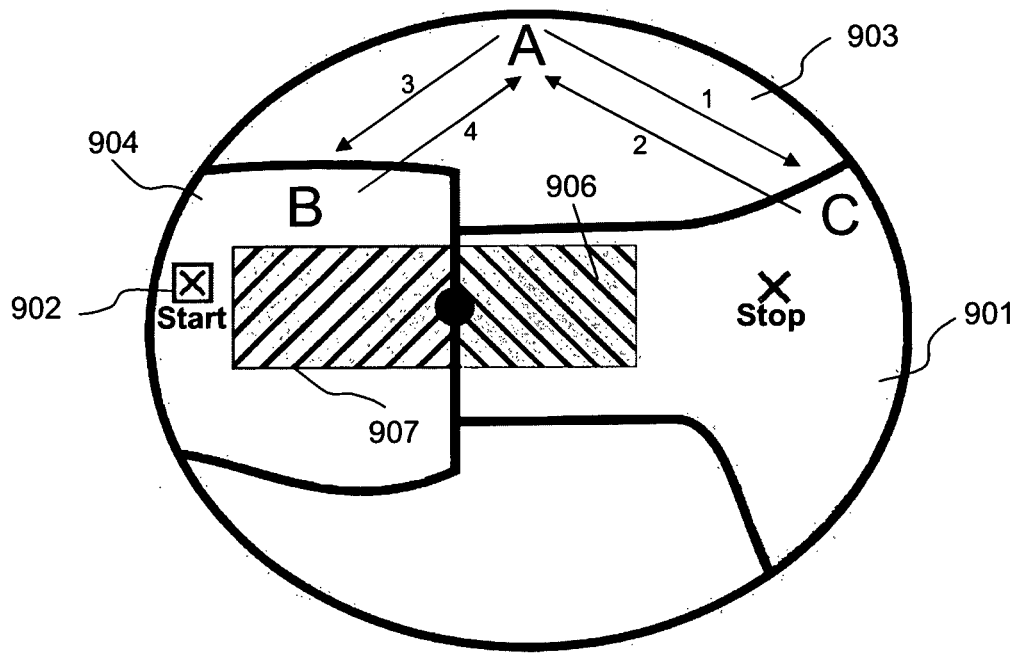
FIGS. 10*a-e* illustrate information flow during the transition shown in FIG. 9.
Figure 10B:
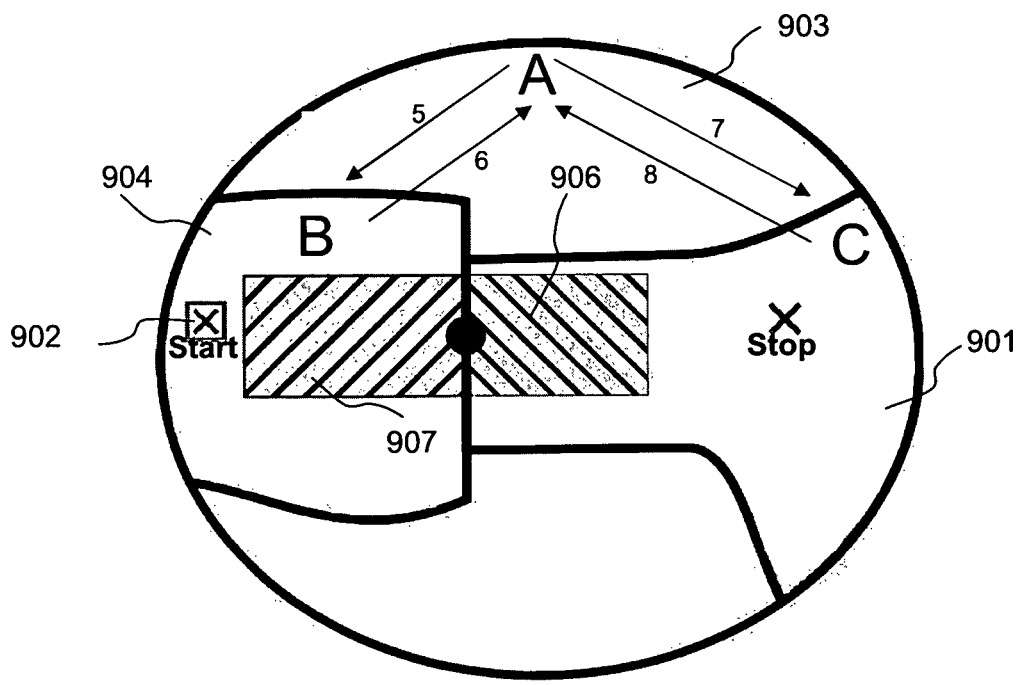
Figure 10C:
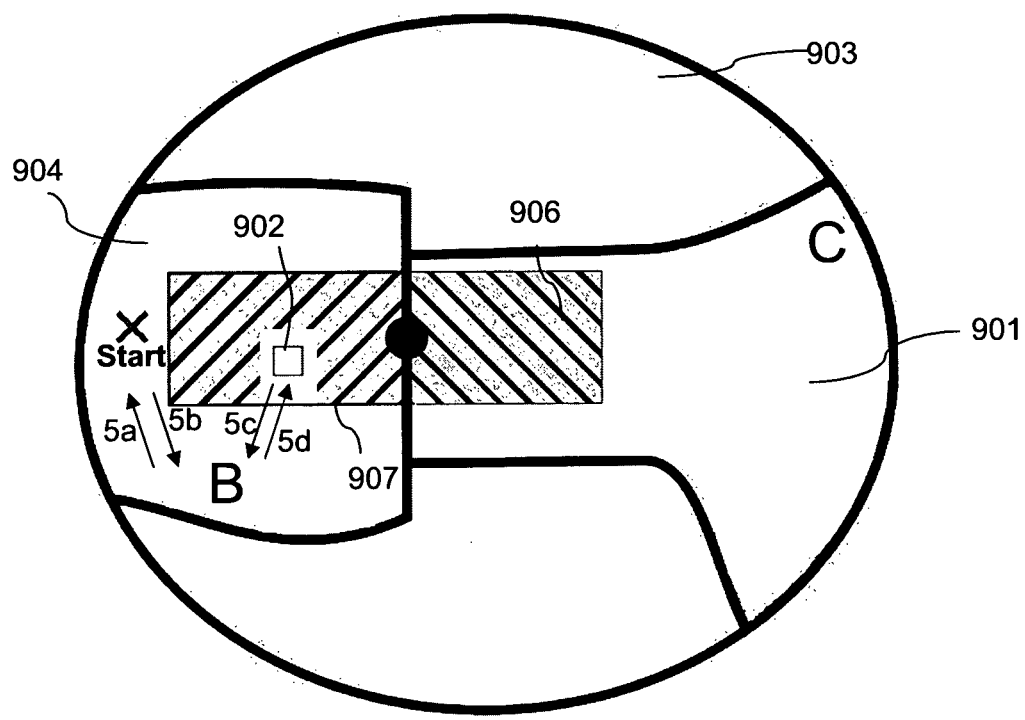
Figure 10D:
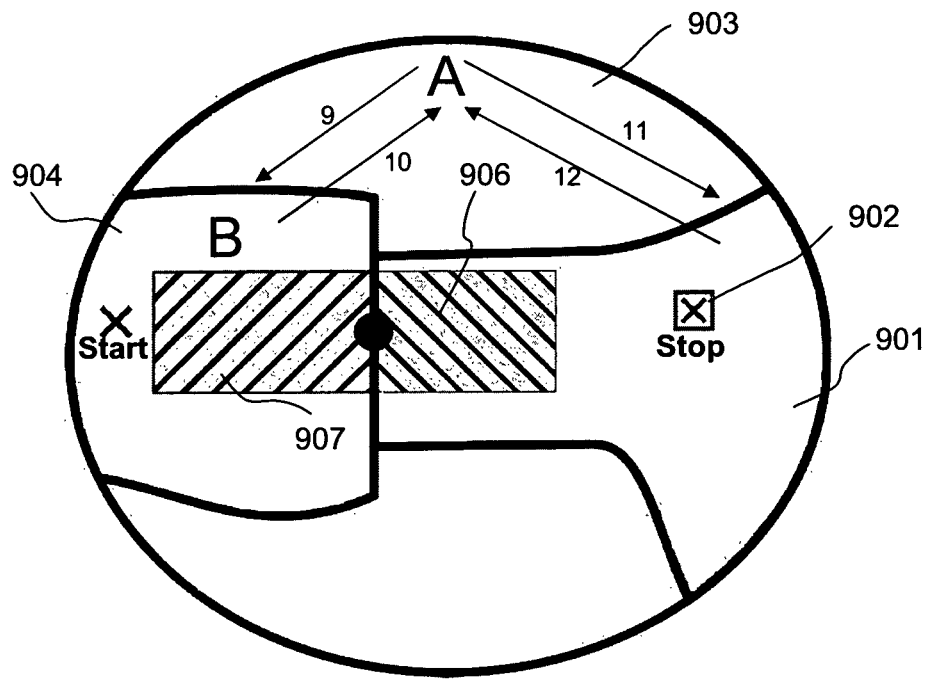

In FIG. 10a the parent xIC 914 sets up the transition. In FIG. 10b the parent xIC 914 hands over the control from the base xIC 912 to the receiver xIC 910 in the transition zones 906 and 907. In FIG. 10c the base xIC 912 controls the transition of the entity 902 into the transition zone 907. In FIG. 10d the base xIC 912 deregisters control of the entity 902, and the receiver xIC 910 takes over the control of the entity 902 for the receiving zone 901.

Figure 10E:
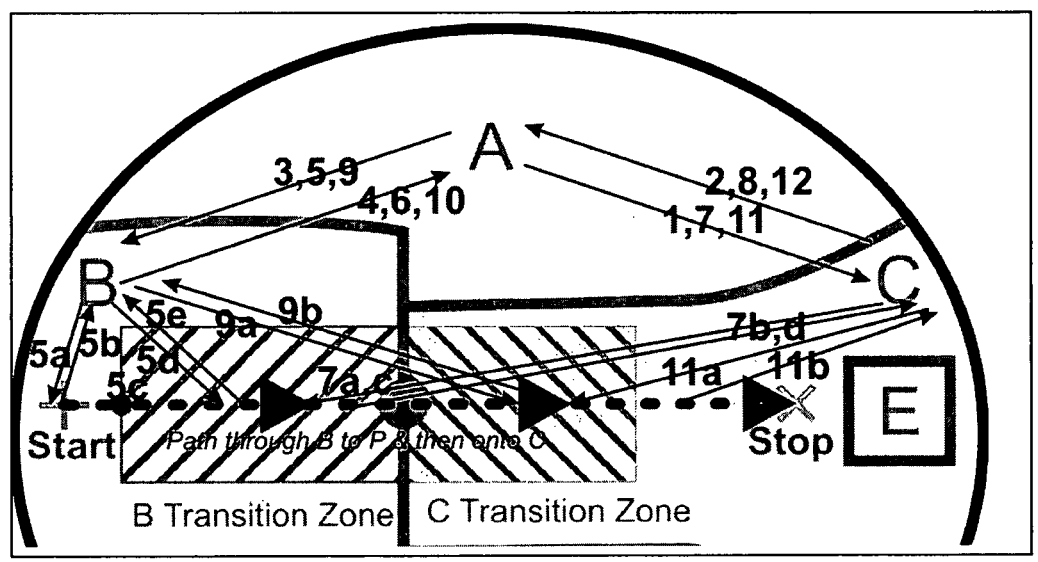

In FIG. 10e all the handshake signals required for the whole transition process are shown.

The process for transition of control follows the sequence:

1. A→C: Query: Can you accept X?
2. C→A: Acknowledgment
3. A→B: Query: Can you release X?
4. B→A: Acknowledgment
5. A→B: Command: Move X to Port P
   a. B→X: Command: trajectory for moving to P, coordinates of transition zone in B.
   b. X→B: Acknowledgment, status updates
   c. X→B: Entered transition zone
   d. B→X: Control non-exclusive, can receive future control messages from C
   e. X→B: Acknowledgment
6. B→A: Status Update: Transition ready
7. A→C: Command: C to send future control commands to X
   a. C→X: Initiation to IoA C (bounds, trajectory zone, etc.), future control trajectories in transition zone, etc.
   b. X→C: Register entry
   c. C→X: Acknowledgment
   d. X→C: Acknowledgment
8. C→A: Status update and acknowledgment
9. A→B: Command: Deregister B
   a. B→X: Deregister control
   b. X→B: Deregistration message/acknowledgment
10. B→A: Acknowledgment
11. A→C: Deregistration acknowledgment
    a. C→X: Authority to execute trajectories beyond the C transition zone
    b. X→C: Acknowledgment
12. C→A: Acknowledgment The transition can also be viewed as a sequence in time, illustrated as follows:

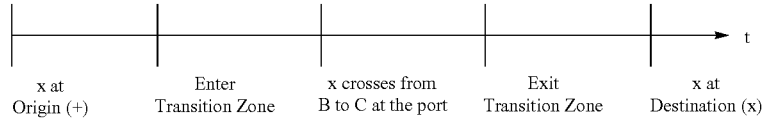

Temporal Sequence for Transitioning Between Islands

The control list on Entity X 902 for this sequence varies as X 902 enters the transition zone 907, crosses the port 905, and exits the transition zone 906. On entry of the transition zone 907, base xIC 912 has primary control, and then has secondary control transitioned to the receiver xIC 910. In this manner, the receiver xIC 910 can communicate and feed forward control before the port 905. After crossing into the receiving IoA 901, the base xIC 912 still maintains communication so as to allow it to deregister. In addition to safety, deregistration is important for the base xIC 912 to free resources that were cleared and allocated to the entity's transition. Thus:

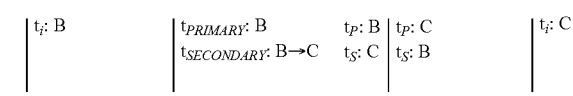

Temporal Sequence for the Control Loss During Transitioning Between Islands

Another aspect of this architecture is that an entity 902 gets future way-points or trajectories for its future planning before full operational control. Once the entity 902 has transitioned to the receiver transition zone 906, there is no need for the base xIC 912 to give trajectories or plans. Thus:

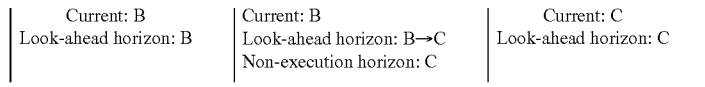

Temporal Sequence for Future Trajectories

Task commands are passed from the Task Planner 308, to the top level of the control hierarchy 610. Two types of movements are relevant:

1. A Mining move—any control that is designed to change the geometry or volumetric content of the mine; and 2. A Standard move—all other control.

The commands are then passed down the hierarchy 610 to the xIC Instance 602 responsible for the entity 902 in question. The xIC Instance 602 converts the task command into a trajectory and sends this to the entity 902 for execution.

3. Example of Mine Site Operation

A much-simplified, representative example of a mine site operation is now described for the purpose of illustrating the MAS architecture 100. However, it is to be understood that the example is given to illustrate key aspects of the MAS functionality rather than to capture all aspects of a real mining operation. The description is provided with reference to FIG. 11, which illustrates an open pit mine having a processing plant 1102 connected by a single road 1104 to a bench 1106 and an adjacent area 1108 where loading is undertaken. Various aspects of the mine site operation are described under the following sub-headings.

3.1. Planning

Figure 12:
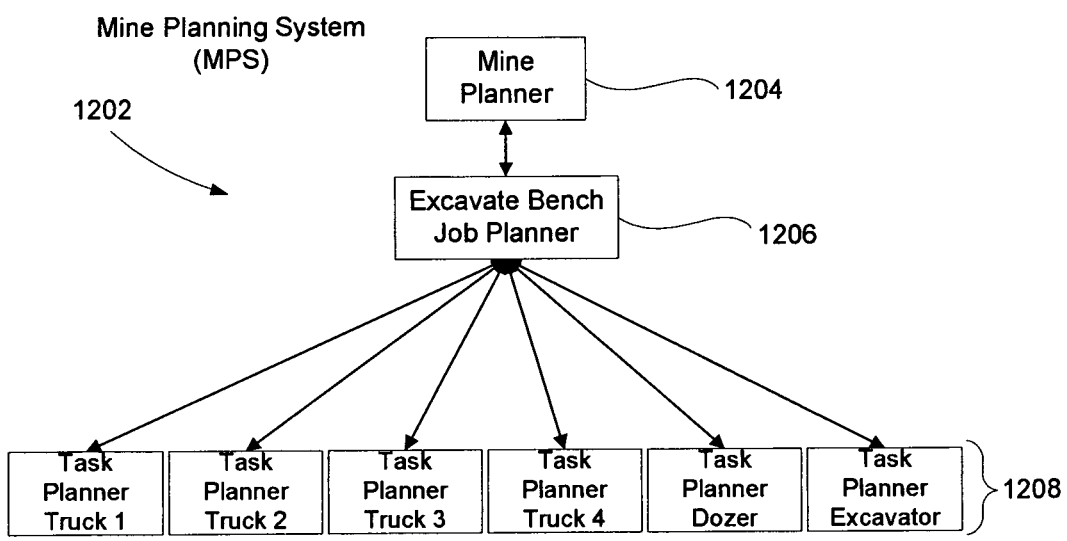
FIG. 12 is a diagrammatic representation of an MPS according to one embodiment of the invention.
Figure 14:
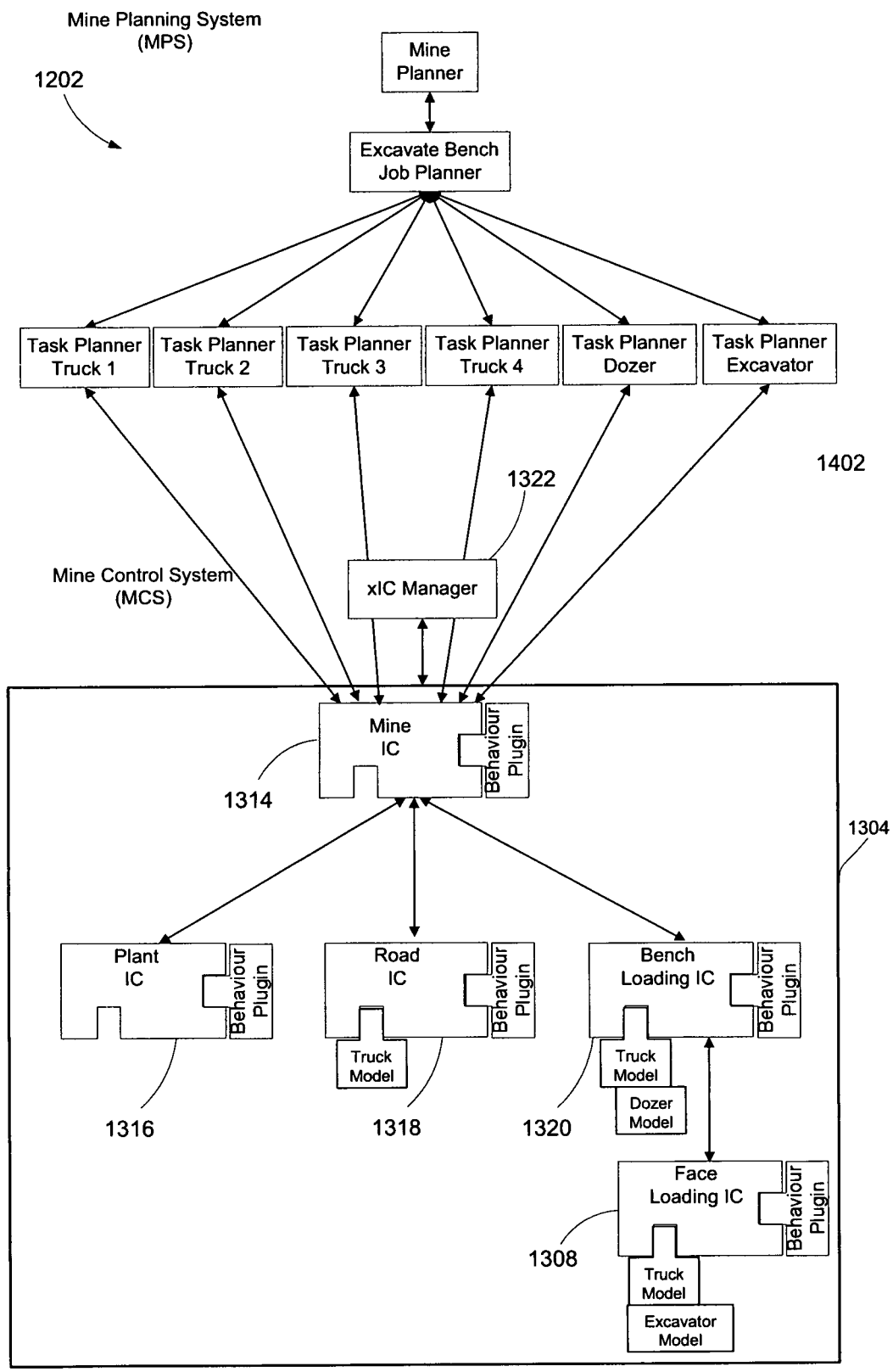
FIG. 14 is a diagrammatic representation of communication between each Task Planner of FIG. 12 and the MCS of FIG. 13.

FIG. 12 illustrates the MPS configuration applicable to this example. Starting from the assumption that the material in the face loading area 1108 is to be mined and transported to the processing plant 1102, a Job Planner 1206 in the MPS 1202 is used to create a job plan to excavate the required volume of material at the appropriate location. The job plan assigns an excavator 1116, four trucks 1112 and a dozer 1114 to the procedure. The entities are assigned permanently by an operator, but the system 100 could also dynamically schedule vehicles depending upon requirements. The Job Planner 1206 then creates a Task Planner 1208 for each entity. The Task Planners 1208 execute the plans through the MCS 1304, as illustrated in FIG. 14. The Task Planners 1208 communicate plans for the respective entities to the top level in the xIC hierarchy 1304, the mine controller 1314; the mine controller 1314 then passes the command down to each subsidiary controller: the plant controller 1316, road controller 1318, bench loading controller 1320 and face loading 1308 controller. The face loading controller 1308 is subsidiary to the bench loading controller 1320. The communication links 1402 also return information from the MCS 1304 to the MPS 1202 relating to task plans (see Table 4).

3.2. Islands of Automation

Figure 11:
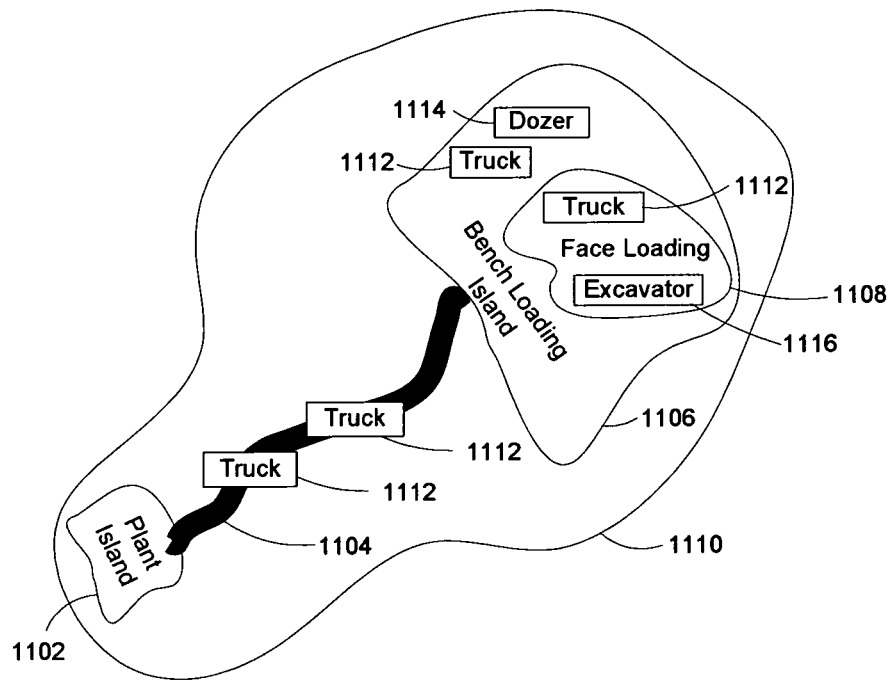
FIG. 11 is a diagrammatic representation of a system according to one embodiment of the invention.
Figure 13:
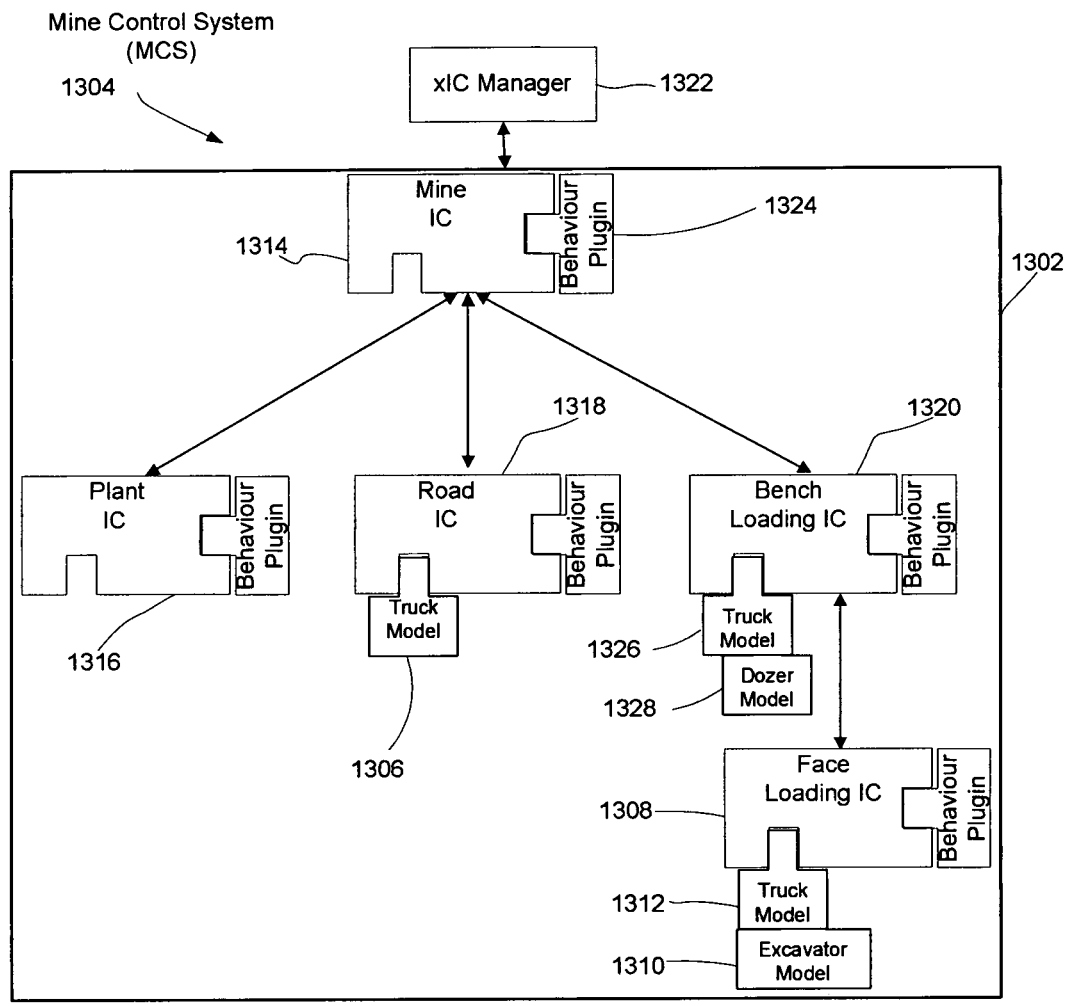
FIG. 13 is a diagrammatic representation of an MCS topology according to one embodiment of the invention.

An IoA is created for each of the geographic regions identified in FIG. 11. At the highest level, the entire mine is an IoA 1110 and, within the mine, the plant 1102, road 1104 and bench 1106 each become a separate IoA. Finally, a face loading IoA 1108 is created within the bench to enclose the excavator 1116 and trucks 1112 at the time of loading. The xIC hierarchy 1302 of the MCS 1304 for this example is shown in FIG. 13. As the mining operations proceed, the geographical boundaries of the face loading island 1108 and the bench loading island 1106 may be varied to match the current location of the operations.

3.3. Controlling the IoAs

The mine IoA has a mine controller 1314. The plant IoA 1102 has a plant controller 1316. The road IoA 1104 has a road controller 1318. The bench loading IoA 1106 has a bench loading controller 1320. The face loading IoA 1108 has a face loading controller 1308.

Each of the IoA controllers as shown in FIG. 13 has a behaviour plug-in (eg plug-in 1324 for the mine IC 1314) that provides parameters in the form, for example, of details of the exact control behaviours, constraints and rules within that geographic region. For example, the priority of entities or road rules around the plant 1102 may differ from those at the bench 1106.

Each of the entities in the mine is registered to the island controller for its geographic region. Thus, these island controllers each have a model plug-in for the vehicles (entities) they are controlling. For example, the face loading IoA 1108 has a model plug-in for both the excavator 1310 and a plug-in for the truck 1312, the road IoA 1104 has a truck plug-in 1306, and the bench loading IoA 1106 has a truck plug-in 1326 and a dozer plug-in 1328. As the plug-ins contain the model for an entity, a single plug-in can be used to control multiple homogeneous entities in the same island.

The key responsibilities of the xIC Manager 1322 are to create, delete, configure and manage the network of xIC instances 1302. These instances are dynamically created and managed based on information received by the xIC Manager 1322, for example jobs or tasks received from the mine planning system.

The deployment configuration for this system desirably has the software for the island controllers running as close as practically possible to the relevant islands. This is so that the controllers will communicate with the entities in the islands with minimal latency and to reduce the need for mine-wide messaging of information that is only relevant to a small region. Example deployments are given as follows:

a) Mine IoA Controller 1314: This may run on a server at the central processing facility for the mine.

b) Plant IoA Controller 1316: A processing facility may be established at the plant to allow the controller to be spatially located at that site.

c) Road IoA Controller 1318: As the road network is distributed throughout the mine, the island controller may desirably run at the central processing facility.

d) Bench IoA Controller 1320: The controller for the bench may run on the excavator 1116. This entity stays in the island whereas trucks and other vehicles are likely to transition regularly.

e) Face Loading IoA Controller 1308: The controller for the face excavation is conveniently run on the excavator, along with the Bench Island Controller 1320. This will allow a permanent wired, high bandwidth communications link between the two.

3.4. Mine Picture Compilation

Figure 15:
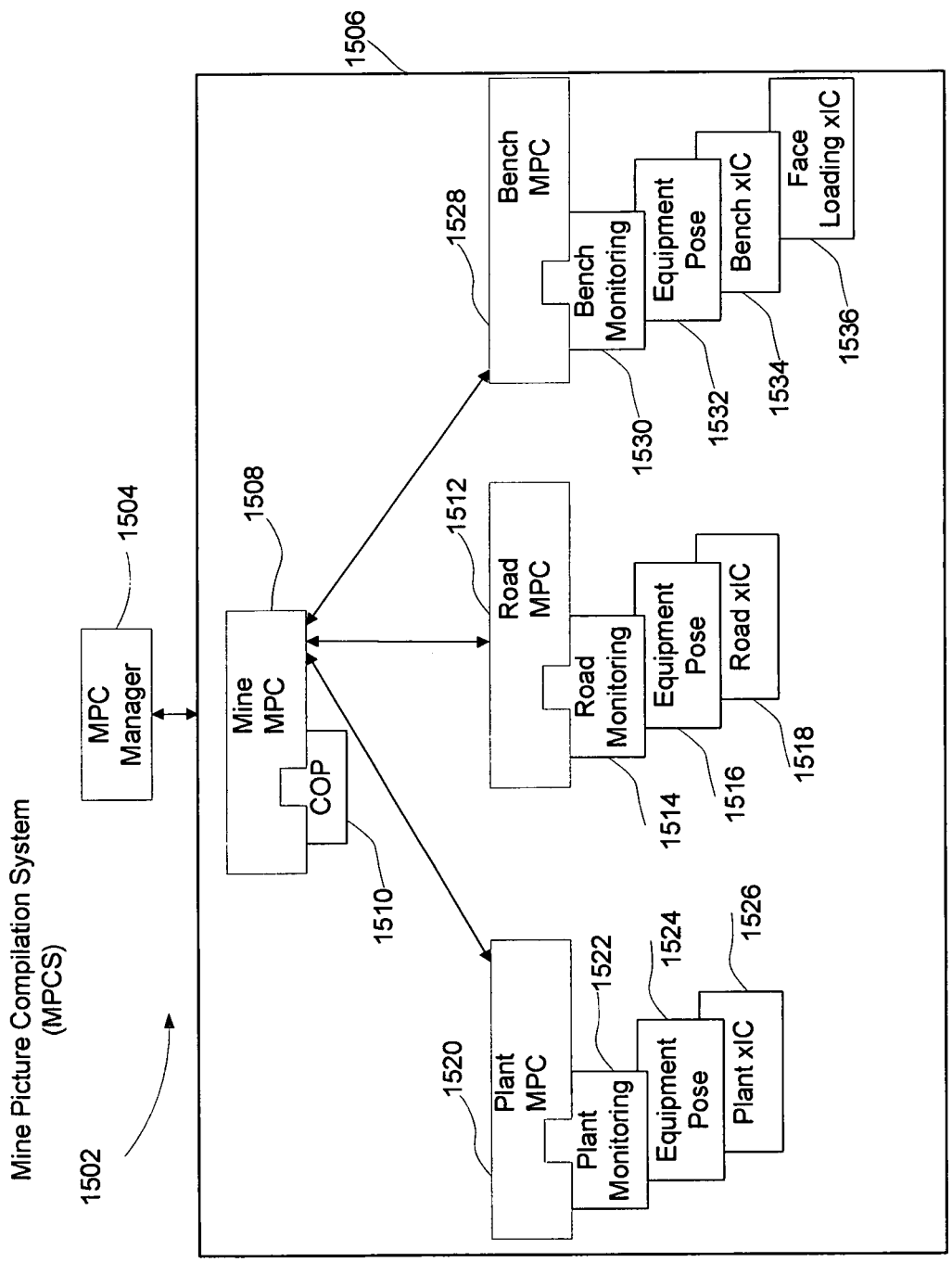
FIG. 15 is a diagrammatic representation of MPCS deployment according to one embodiment of the invention.

FIG. 15 shows the MPCS 1502 for this example. One possible deployment configuration for this system will have the various MPC devices as illustrated in FIG. 15 and referred to as follows:

a) Mine MPC 1508: This MPC device is the core of the MPC hierarchy 1506 and contains the global mine operating picture. It may be run at the central processing facility with a wired, high bandwidth connection to the Mine Island Controller 1314. In this example, it has only a single plug-in 1510 connected which enables systems and operators external to the MPCS 1502 to access fused MPC information.

b) Road MPC 1512: The road MPC device extracts information for the road areas. It may be run at the central processing facility with a wired, high bandwidth connection to the Road Island Controller 1318. It contains model plug-ins with the following functions:

1. Road monitoring 1514: Update the in-ground geometry model with road surface data from vehicles;
2. Equipment Pose 1516: Update the equipment model with vehicle pose information;
3. Road xIC 1518: Enable an interface to the Road Island Controller 1318. This provides the island controller 1318 with access to the fused MPC information, and allows the road MPC 1512 to access trajectory information from the controller 1318.

c) Plant MPC 1520: The plant MPC device extracts information for the plant region. It may be run on a processing facility located at the plant, with a wired, high bandwidth connection to the Plant Island Controller 1316. It contains model plug-ins with the following functions:

1. Plant monitoring 1522: Update the out-of-ground model with real-time assay information from the plant;
2. Equipment Pose 1524: Update the equipment model with vehicle pose information;
3. Plant xIC 1526: Enable an interface to the Plant Island Controller 1316. This provides the island controller 1316 with access to the fused MPC information, and allows the plant MPC 1520 to access trajectory information from the controller.

d) Bench MPC 1528: The Bench MPC extracts information for the bench region. It may be run on a processing facility on the excavator with a wired, high bandwidth connection to both the Bench Loading Island Controller 1320 and the Face Loading Island Controller 1308. It contains model plug-ins with the following functions:

1. Bench monitoring 1530: Use bucket scanning to update the in-ground and out-of-ground models as material is excavated.
2. Equipment Pose 1532: Update the equipment model with vehicle pose information.
3. Bench xIC 1534: Enable an interface to the Bench Loading Island Controller 1320. This provides the island controller 1320 with access to the fused MPC information, and allows the bench MPC 1528 to access trajectory information from the controller 1320.
4. Face Loading xIC 1536: Enable an interface to the Face Loading Island Controller 1308. This provides the island controller 1308 with access to the fused MPC information, and allows the bench MPC 1528 to access trajectory information from the controller 1308.

The bench 1106 and face loading 1108 islands in this example are configured to operate on the same MPC instance 1528, reducing the number of MPCs running and hence the complexity of the system. However, an alternative strategy would be to have an extra MPC instance for the face loading island 1108 and accept the extra computing and complexity requirements.

3.5. System Integration

Figure 16:
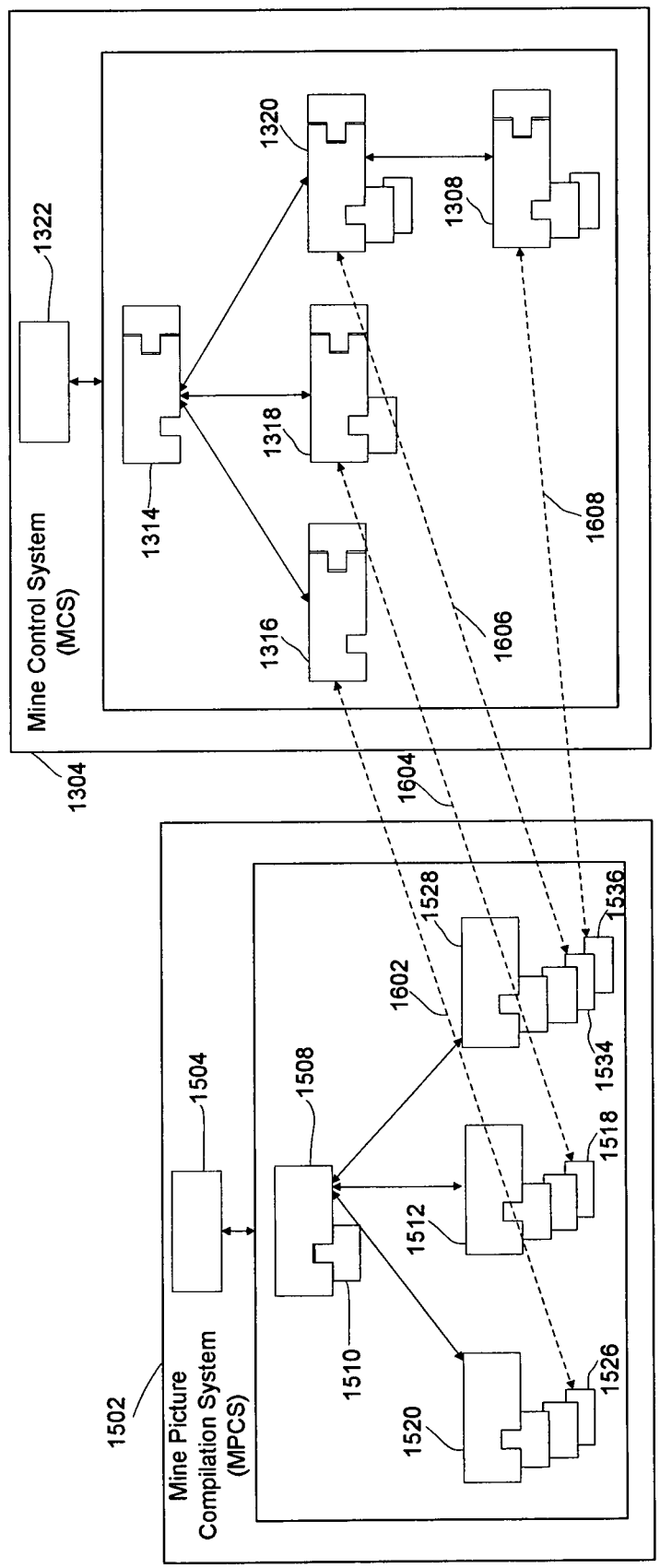
FIG. 16 illustrates control communications to an MPCS plug-in of FIG. 15 in the MCS of FIG. 13.

FIG. 16 illustrates connection links between the MPCS 1502 and MCS 1304. When each of the xIC Instances is created, it registers a xIC plug-in with an MPC instance.

The plant xIC 1316 registers the plant xIC plug-in model 1526 with the plant MPC 1520 over a link 1602. The road xIC 1318 registers the road xIC plug-in model 1518 with the road MPC 1512 over a link 1604. The bench loading xIC 1320 and the face loading xIC 1308 register the bench xIC plug-in model 1534 and the face loading xIC plug-in model 1536 with the bench MPC 1520 over links 1606 and 1608 respectively.

It is through these links that the controllers receive the latest state information from each MPC instance and transmits planned trajectory information to each MPC instance. In this example, both the Bench 1106 and Face Loading 1108 IoAs are connected to the same MPC instance 1528. As both of these island controllers are deployed on the same entity, the excavator, both can use a common MPC instance 1528. Importantly, the MPC instance 1528 should be deployed at the same physical location as the controllers 1320, 1308 and connected through a hardwired link to accommodate both communications links 1606, 1608, as these form part of a control loop.

Figure 17:
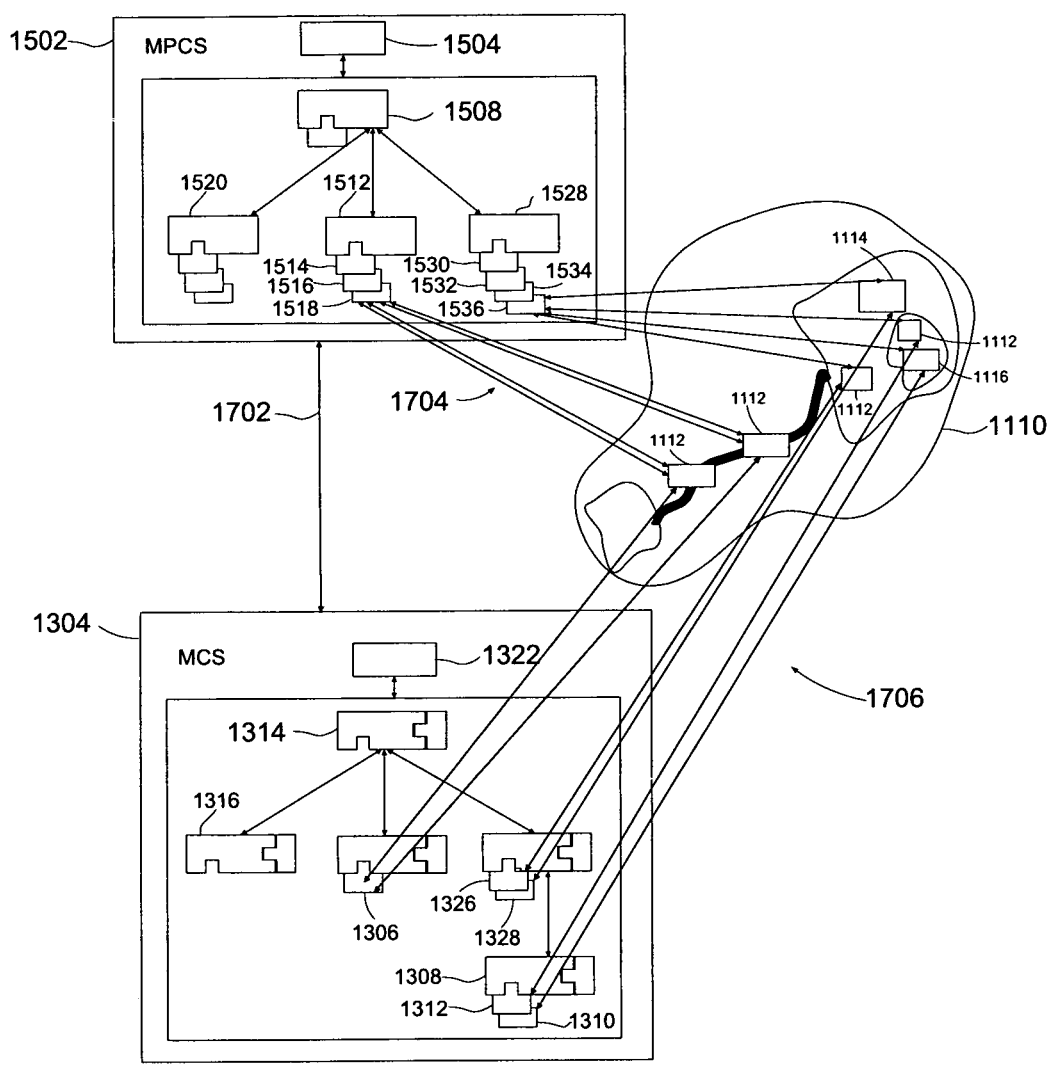
FIG. 17 illustrates communication between the MPCS of FIG. 15, the MCS of FIG. 13 and mine equipment shown in FIG. 11.

FIG. 17 illustrates the control loop between the MCS 1304, entities in the mine 1110 (including trucks 1112, a dozer 1114 and an excavator 1116) and the MPCS 1502. Communications between the MPCS 1502 and MCS 1304 as illustrated in FIG. 16 are summarised as a single link 1702 for clarity.

xIC entity plug-in models that communicate control information to the entities include the truck plug-ins 1306, 1326, 1312, the dozer plug-in 1328 and the excavator plug-in 1310. This information is communicated across communication links 1706 Information from the entities is then sent to the MPC plug-ins: the road mapping plug-in 1514, the equipment pose plug-in 1516, the road xIC plug-in 1518, the bench monitoring plug-in 1530, the equipment pose plug-in 1532, the bench xIC plug-in 1534 and the face loading xIC 1536. This information is sent over communication links 1704 between the entities and the MPC plug-ins, and is used for fusion into the appropriate MPC model. This demonstrates the control loop between the MCS 1304, entities in the mine and the MPCS 1502.

Figure 18:
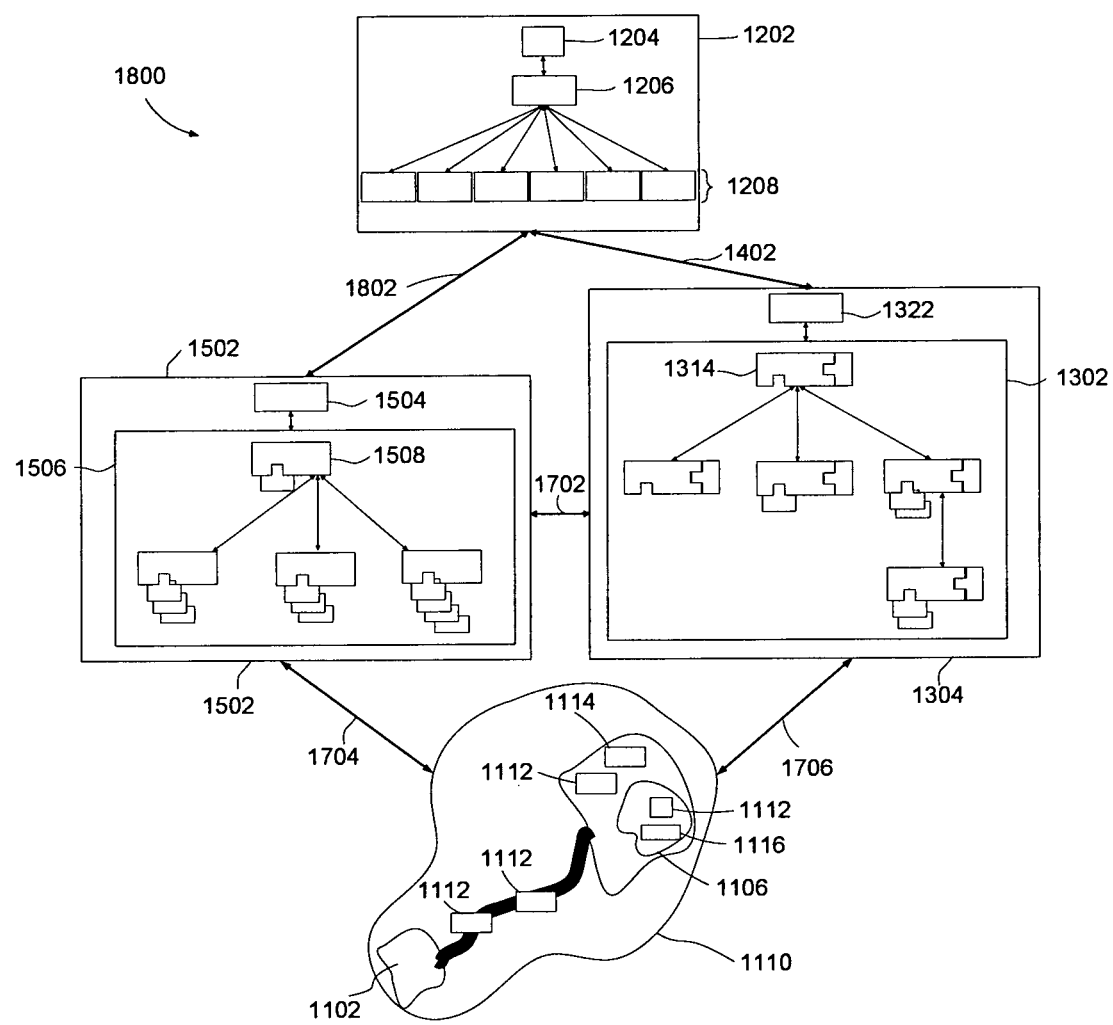
FIG. 18 is a diagrammatic representation of a configuration of the MAS according to the components described in FIGS. 11-17.

FIG. 18 illustrates how all elements of the MAS 1800 in this example form an integrated system. The island of automation that is defined by the whole mine site 1110 is controlled by the MAS 1800. The MAS 1800 comprises the MPS 1202, the MCS 1304 and the MPCS 1502. Communication occurs between the MPS 1202 and the MCS over bidirectional communication links 1402 as shown in FIG. 14. Communication occurs between the MPS 1202 and the MPCS 1502 over bidirectional communication links 1802 providing the MPCS 1502 with information about managing the MPC instances and about task plans of the entities and providing the MPS 1202 with information about the MPCS configuration and with information from the in-ground model, the out-of-ground model and the equipment model (see Table 3). Communication occurs between the MCS 1304 and the MPCS 1502 over communication links 1702 as described with reference to FIG. 16: the MCS 1304 receives information about the MPC instances and information from the equipment model, in-ground model and out-of-ground model; the MPCS 1502 received information about the MCS configuration, the trajectory plans of entities and the status of tasks (see Table 5).

The embodiment illustrated in the Figures and described above relates to a mining application. It will be appreciated that there are many other fields of application relevant to integrated autonomous control, including forestry and agriculture. The automation system of FIG. 2 may be used to control autonomous operation of equipment in various applications where a plurality of localised zones having operation-defined geographical boundaries are established within a region.

In the mining application, the term "in-ground information" refers to geometrical, geophysical and geological information about in-ground material, along with information about mining activities that have occurred or are to occur prior to the extraction of the material. The in-ground or unexcavated material is material that has not been excavated yet. Geometrical information represents information about the location and the geometry of the mine, benches, etc. It also includes information about the location of existing or to-be-drilled holes and their dimensions. This constitutes a drill pattern. Furthermore, geometrical information can also have associated information relating to quantity and composition of explosives to be provided in the holes. Using the in-ground information, it is possible to estimate quantity and stocks of in-ground material. In-ground information also comprises chemical and mechanical properties of the different zones of the mine. All in-ground information is fused to form an in-ground model.

In an agricultural application the term "in ground information" may relate to the soil and economically useful plants or crops in a region of interest. The in-ground model obtains, through sensing, an integrated picture of the geometry, chemical composition, and crop health over the required area. More generally, the term "in-ground information" falls into the class of "pre-extraction", "pre-intervention" or "pre-processing" information and refers to information describing a region at some starting reference point, or a relative starting reference point within a dynamic process subject to continual re-evaluation. The region resource may be, for example, a mine, an agricultural resource or a forestry resource that is subject to intervention or processing by the equipment referred to below. In this broader sense the "in-ground information" is not limited literally to information relating to the ground, but may, for example refer to a marine resource.

In this description a second type of information is termed "out-of-ground information". In the mining application the "out-of-ground information" refers to information about the extracted or out-of ground material including stockpiles and material in process. This information includes, but is not limited to, geophysical, chemical and grade of the out-of-ground material in addition to its location within the mine. Using the out-of-ground information, it is possible to estimate the stocks and quantity of out-of-ground material. The out-of-ground information is fused to form an out-of-ground model.

In an agricultural application the out-of-ground information may, for example, describe a harvested crop. More generally, the out-of-ground information falls into the class of "post-extraction", "post-processing" or "post-intervention" information that describes material extracted or harvested from the environment described by the in-ground (pre-extraction) information. In some applications the out-of-ground label does not related literally to the ground, but may, for example, have reference to a harvested marine resource.

The expression "equipment information" refers to information relating to the pieces of equipment used in a resource-processing application. The equipment is instrumental in transferring material from the in-ground or pre-processing environment to the out-of-ground or post-processing environment. In the context of a mining operation, for example, "equipment information" refers to information relating to the pieces of equipment used in a mine and to its operators. The equipment information includes, but is not limited to, the number, the location, the status, the disposition, and the type of the piece of equipment. It also includes scheduling and logistic information. All equipment information is fused to form an equipment model.

The term "automatic" refers to a system or process that executes a specific well-defined task that is often narrowly defined. "Automatic" implies following a set of well-defined rules and reacting in a defined way to a defined stimulus. "Automated systems" are those that have some automatic components or properties.

The term "autonomous" refers to systems that are more complex as the systems are able to respond to unknown stimuli and can function without a complete knowledge of their environments. Typically, an autonomous system does not require human intervention to respond to at least some unpredicted changes in its environment.

The three models relating to in-ground, out-of-ground, and equipment information, may be used to form an overall integrated picture for use in monitoring and exploiting an environment such as a mine. The models may also be applied to the fusion of information for estimation in forestry and agriculture applications, for example the fusion of in-ground information such as soil properties with out-of-ground information such as crop or harvest data. The equipment or operation units in this example might include tractors, ploughs and other agricultural equipment.

In a similar manner, fusion of in-ground information may also be used for drainage or irrigation applications. Further applications may also include the fusion of information for estimating properties of the ocean or other liquid bodies. Maritime examples include the use of the in-ground model to estimate properties such as ocean temperature and salinity. "Out-of-ground" type estimates may relate to any marine resource including fish or minerals extracted from the ocean. In marine applications the equipment entities may, for example, include fishing vessels, nets and submarines, and the "in-ground" model may, for example, include sonar modelling.

The term "fusing" refers in this description to combining information from multiple sources to create a data model or combining new information with already existing information of a data model to update this data model. The multiple sources can be either homogeneous or heterogeneous sources. The information from the multiple sources typically has different characteristics, for example the accuracy of the data, but provides information about the same measured parameters, for example coordinates describing the position of an object. One reason for fusing information from heterogeneous sources, for example multiple sensors, is to improve the accuracy of the value(s) estimated from the measured values. The fusion of information can also refer to updating old information with new information, for example, replacing a location of a vehicle by its new position. The fusion of information may make use of fusion algorithms. One realisation of the post-processing, or out-of-ground, and equipment models may use a Kalman filter, information filter or particle filter for information fusion. However, any other fusion algorithm may also be applicable.

It will be understood that the invention disclosed and defined in this specification extends to all alternative combinations of two or more of the individual features mentioned or evident from the text or drawings. All of these different combinations constitute various alternative aspects of the invention.

TABLE 12

List of acronyms

| | |
|---|---|
| AHT | Autonomous Haul Truck |
| AP | Access Point |
| BIF | Banded Iron Formation |
| CAES | Computer Aided Earthmoving System |
| COP | Common Operating Picture |
| HLSA | High Level System Architecture |
| ID | Identification |
| IoA | Island of Automation |
| JP | Job Planner |
| MAS | Mine Automation System |
| MCS | Mine Control System |
| MP | Mine Planner |
| MPC | Mine Picture Compilation |
| MPCS | Mine Picture Compilation System |
| MPS | Mine Planning System |
| OEM | Original Equipment Manufacturer |
| PVA | Position, Velocity, Attitude |
| ROC | Remote Operations Centre |
| TP | Task Planner |
| UML | Unified Modelling Language |
| VPN | Virtual Private Network |

TABLE 13

Control system terminology

| | |
|---|---|
| Island of Automation or Island of Autonomy (IoA): | A spatial region whose boundaries are well defined and which contains specific (discrete) ports for traffic. |
| xIC: | A generic module for controlling and coordinating actions within an island of automation. |
| Entity: | A piece of equipment, machine, person or other "asset" operating in the mine site. |
| Parent: | The high-level xIC responsible for the overall task |
| Child: | Recursive xIC modules that are started and controlled by a parent xIC. |
| Base (B): | The current possessor of an entity. |
| Collector or Receiver (C): | The recipient of an entity |
| Control List: | For an entity, the list of ICs that it is listening to. Note that listening does not necessarily imply execution. Execution is determined based on a ranking mechanism. |
| Transition Zone: | A user bounded, port location between IoAs for entity transfer and control transition. It has a continuous area in which an area an entity is allowed to communicate simultaneously with the xIC's. It covers both the xIC's involved in the transfer and straddles the border of their IoAs. Energetic classification of commands: |
| −active: | commands the remove energy from the entity (e.g., braking); |
| passive: | commands that do not alter the energy state of the entity (e.g., steering) or; |
| +active: | commands that add energy to the entity (e.g., accelerating) |

What is claimed is:

1. A computer-implemented method of generating a data representation of a geographical region as an adjunct to conducting autonomous operations within the region, the method comprising:
   a) receiving information specifying a hierarchy of localized zones having operation-defined geographical boundaries within the region, the hierarchy determined by respective spatial locations of the localized zones in the region;
   b) receiving heterogeneous data descriptive of the region from a plurality of sensors, the heterogeneous data including data relating to a mobile equipment unit; and
   in a processing system configured with a hierarchy of model compilers corresponding to the localized zones, performing the operations of:
   c) associating the received data with respective localized zones, and associating received data relating to the mobile equipment unit with a localized zone in which the mobile equipment unit is located;
   d) fusing the received data associated with the respective localized zones into data representations of the plurality of localized zones;
   e) integrating the data representations of the localized zones into a common data representation of the geographical region, wherein the common data representation is generated as an adjunct to conducting autonomous operations within the region; and
   f) providing information from the data representations to a control system that controls the autonomous operations within the region.

2. The method according to claim 1 wherein the autonomous operations are for the extraction of at least one resource from the region and wherein the data representations of the localized zones and the common data representation of the geographic region each comprise models selected from the group consisting of:
   a pre-extraction model descriptive of the zone or region and the at least one resource within the zone or region;
   an equipment model descriptive of equipment operating in the zone or region; and
   a post-extraction model descriptive of extracted material within the zone or region.

3. The method of claim 2, wherein the pre-extraction model comprises a spatial description of the zone or region.

4. The method of claim 2, wherein the pre-extraction model comprises an estimate of the distribution of the at least one resource in the zone or region.

5. The method of claim 1 comprising defining a hierarchical structure for the data representations corresponding to a hierarchical organization of the localized zones.

6. The method of claim 1 comprising receiving information specifying updated boundaries of at least one localized zone.

7. The method of claim 1 wherein the geographic region comprises a mine.

8. The method of claim 2 wherein the received data comprises information descriptive of the at least one resource and selected from the group consisting of chemical, physical, geological, geophysical, mineralogical and contextual properties of the resource.

9. The method of claim 8 wherein the pre-extraction model comprises a description of a distribution and grade of the at least one resource.

10. The method of claim 1 wherein the geographic region is selected from the group consisting of an agricultural region, a forestry region and a marine region.

11. A system for generating a model of an environment in which a plurality of equipment units are deployed for the extraction of at least one resource from the environment, the system comprising:
   a computing system with at least one processing unit and at least one non-transitory computer-readable storage medium storing computer-executable code for execution by the at least one processing unit,
   wherein the environment is divided into a hierarchy of localized zones having operation-defined geographical boundaries, the hierarchy determined by respective spatial locations of the localized zones in the environment;

wherein the execution of the computer-executable code provides:

a managing unit to configure a plurality of model compilers formed in a hierarchy corresponding to the localized zones, each model compiler comprising modelling units selected from the set consisting of:

a) a pre-extraction modelling unit configured to receive data from a first plurality of heterogeneous sensors and to fuse the data into a pre-extraction model descriptive of the corresponding localized zone;

b) an equipment modelling unit configured to receive equipment data relating to one or more of the equipment units operating in the corresponding localized zone and to combine the equipment data into an equipment model; and c) a post-extraction modelling unit configured to receive data from a second plurality of sensors and to fuse the data into a post-extraction model descriptive of extracted material; and wherein the system provides information from the plurality of model compilers to a control system that controls the autonomous operations within the region.

12. The system of claim 11 comprising a model compiler corresponding to the environment and configured to integrate the models of the model compilers corresponding to the localized zones into a common representation of the environment.

13. The system of claim 11 wherein the model compilers corresponding to the localized zones comprise interface modules to enable
communication between the model compiler and data systems of equipment operating in the corresponding localized zone.

14. The system of claim 11, wherein the pre-extraction model comprises:
a spatial description of the zone or region; and
an estimate of the distribution of the at least one resource in the zone or region.

15. The system of claim 11, wherein the post-extraction modelling unit is configured to receive data from the pre-extraction modelling unit and from the equipment modelling unit for reconciling material conservation during the extraction of the at least one resource from the environment.

* * * * *